United States Patent [19]

Thomas et al.

[11] Patent Number: 5,540,673
[45] Date of Patent: Jul. 30, 1996

[54] REFASTENABLE MECHANICAL FASTENING SYSTEM

[75] Inventors: Dennis A. Thomas, Cincinnati; David J. K. Goulait, West Chester; Robert G. Cox, Jr., Cincinnati, all of Ohio

[73] Assignee: The Procter & Gamble Company, Cincinnati, Ohio

[21] Appl. No.: 381,025

[22] Filed: Jan. 31, 1995

Related U.S. Application Data

[60] Continuation of Ser. No. 979,726, Nov. 20, 1992, abandoned, which is a division of Ser. No. 632,283, Dec. 21, 1990, Pat. No. 5,180,534, and a continuation-in-part of Ser. No. 668,817, Mar. 7, 1991, Pat. No. 5,230,851, which is a continuation of Ser. No. 305,354, Jan. 31, 1989, abandoned.

[51] Int. Cl.$^6$ ................................................. A61F 13/15
[52] U.S. Cl. ..................... 604/391; 24/442; 128/DIG. 15; 2/912
[58] Field of Search ....................... 604/391; 24/442–452; 128/DIG. 15; 2/920, 912–919

[56] References Cited

U.S. PATENT DOCUMENTS

| | | | |
|---|---|---|---|
| 392,363 | 11/1888 | Riggs . | |
| 569,213 | 10/1896 | Lehnig . | |
| 625,022 | 5/1899 | Crist . | |
| 2,717,437 | 9/1955 | Mestral | 28/72 |
| 3,057,354 | 10/1962 | Roberts et al. . | |
| 3,130,111 | 4/1964 | Izumi | 161/48 |
| 3,147,528 | 9/1964 | Erb | 24/204 |
| 3,266,113 | 8/1966 | Flanagan, Jr. | 24/204 |
| 3,426,400 | 2/1969 | Lauro | 24/255 |
| 3,461,513 | 8/1969 | Girard et al. | 24/204 |
| 3,536,518 | 10/1970 | Drelich | 117/38 |
| 3,550,223 | 12/1970 | Erb | 24/204 |
| 3,550,837 | 12/1970 | Erb | 229/45 |
| 3,557,407 | 1/1971 | Lemelson | 425/71 |
| 3,562,044 | 2/1971 | Erb | 156/155 |
| 3,594,863 | 7/1971 | Erb | 18/5 |
| 3,594,865 | 7/1971 | Erb | 18/5 |
| 3,629,032 | 12/1971 | Erb | 156/196 |
| 3,643,316 | 2/1972 | Girard et al. | 29/400 |
| 3,675,571 | 7/1972 | Vertegaal . | |
| 3,708,382 | 1/1973 | Erb | 161/48 |
| 3,708,833 | 1/1973 | Ribich et al. | 24/204 |
| 3,943,981 | 3/1976 | De Brabander | 139/391 |
| 4,056,593 | 11/1977 | de Navas Albareda | 264/145 |
| 4,169,303 | 10/1979 | Lemelson | 24/204 |
| 4,198,734 | 4/1980 | Brumlik | 24/204 |
| 4,216,257 | 8/1980 | Schams et al. | 428/93 |

(List continued on next page.)

FOREIGN PATENT DOCUMENTS

| | | |
|---|---|---|
| 2027159 | 7/1991 | Canada . |
| 0276970 | 8/1988 | European Pat. Off. . |
| 0325473A1 | 7/1989 | European Pat. Off. . |
| 0353972 | 2/1990 | European Pat. Off. . |
| 0381087 | 8/1990 | European Pat. Off. . |
| 0388681 | 9/1990 | European Pat. Off. . |
| 0476992A1 | 3/1992 | European Pat. Off. . |
| 0491347A1 | 6/1992 | European Pat. Off. . |
| 1551245 | 12/1968 | France . |
| 2432108 | 12/1980 | France ........... 3/16 |
| 55/137942 | 10/1980 | Japan . |
| 2233876 | 1/1991 | United Kingdom . |
| WO87/06522 | 11/1987 | WIPO . |

*Primary Examiner*—Robert A. H. Clarke
*Attorney, Agent, or Firm*—Steven W. Miller; E. Kelly Linman; Jacobus C. Rasser

[57] ABSTRACT

The invention is a refastenable mechanical fastening system, made of free formed prongs joined to a substrate. The prongs taper and are nonperpendicularly oriented relative to the plane of the substrate. The prongs also have an azimuthal angle relative to the machine direction of the substrate. Each prong has an engaging means projecting laterally from the periphery of the prong. The free formed prongs are manufactured by the process of depositing liquid material onto a moving substrate, stretching the liquid material in a direction parallel to the plane of the substrate, severing the stretched material to form the distal end and engaging means of the prong, and imparting an azimuthal angle to the prong. The advantageous usage of the fastening system in an article of manufacture, such as a disposable absorbent garment, specifically a diaper, is also disclosed.

19 Claims, 5 Drawing Sheets

U.S. PATENT DOCUMENTS

| | | | |
|---|---|---|---|
| 4,307,493 | 12/1981 | Ochiai | 24/204 |
| 4,330,907 | 5/1982 | Ochiai | 24/204 |
| 4,454,183 | 6/1984 | Wollman | 428/92 |
| 4,462,784 | 7/1984 | Russell | 425/223 |
| 4,463,486 | 8/1984 | Matsuda | 28/161 |
| 4,532,157 | 7/1985 | Schmidt et al. | 427/262 |
| 4,562,099 | 12/1985 | Hichcliffe | 427/282 |
| 4,587,152 | 5/1986 | Gleichenhagen | 428/195 |
| 4,672,893 | 6/1987 | Mammarella, Sr. | 101/170 |
| 4,699,622 | 10/1987 | Toussant et al. | 604/389 |
| 4,725,221 | 2/1988 | Blanz | 425/575 |
| 4,776,068 | 10/1988 | Smirlock et al. | 24/442 |
| 4,794,028 | 12/1988 | Fischer | 428/100 |
| 4,829,641 | 5/1989 | Williams | 24/587 |
| 4,846,815 | 7/1989 | Scripps . | |
| 4,869,724 | 9/1989 | Scripps . | |
| 4,876,982 | 10/1989 | Claassen . | |
| 4,884,323 | 12/1989 | Provost et al. | 24/442 |
| 4,894,060 | 1/1990 | Nestegard | 604/391 |
| 4,938,835 | 7/1990 | Ludwig | 118/68 |
| 4,963,140 | 10/1990 | Robertson . | |
| 4,973,326 | 11/1990 | Wood et al. | 604/391 |
| 4,984,339 | 1/1991 | Provost et al. | 24/442 |
| 5,013,498 | 5/1991 | Froeschke . | |
| 5,019,065 | 5/1991 | Scripps . | |
| 5,040,275 | 8/1991 | Eckhardt et al. . | |
| 5,053,028 | 10/1991 | Zoia et al. . | |
| 5,058,247 | 10/1991 | Thomas et al. | 24/450 |
| 5,116,563 | 5/1992 | Thomas et al. | 156/66 |
| 5,122,219 | 6/1992 | Ludwig | 156/244.17 |
| 5,131,119 | 7/1992 | Murasaki et al. . | |
| 5,135,522 | 8/1992 | Fahrenkrug et al. . | |
| 5,176,671 | 1/1993 | Roessler et al. | 604/391 |
| 5,180,534 | 1/1993 | Thomas et al. . | |
| 5,230,851 | 7/1993 | Thomas | 604/391 |
| 5,325,569 | 7/1994 | Goulait et al. | 24/448 |
| 5,392,498 | 2/1995 | Goulait et al. | 24/452 |

REFASTENABLE MECHANICAL FASTENING SYSTEM

This is a continuation of application Ser. No. 07/979,726, filed on Nov. 20, 1992 now abandoned; which is a divisional of application Ser. No. 07/632,283, filed on Dec. 21, 1990 now U.S. Pat. No. 5,180,534; and is a continuation-in-part of application Ser. No. 07/668,817, filed on Mar. 7, 1991 now U.S. Pat. No. 5,230,851; which is a continuation of application Ser. No. 07/305,354, filed on Jan. 31, 1989 now abandoned.

FIELD OF THE INVENTION

The present invention relates to refastenable mechanical fastening systems, more particularly to fastening systems having free formed prongs and the process of manufacturing such fastening systems.

BACKGROUND OF THE INVENTION

Refastenable mechanical fastening systems are well known in the art. Typically, such fastening systems involve two major components, a prong which is joined to a substrate and engages with a complementary second component, the receiving surface. A projection of the prong of the fastening system penetrates the receiving surface and either engages or intercepts strands or fibers of the receiving surface. The resulting mechanical interference and physical obstruction prevent removal of the fastening system from the receiving surface until the separation forces exceed either the peel or shear strength of the fastening system.

Presently, refastenable mechanical fastening systems are made by at least two general methods. One method requires a plurality of filaments, each of which may be formed into two prongs. Examples of fastening systems produced by this method are shown in U.S. Pat. No. 2,717,437, issued Sep. 13, 1955 to de Mesteral and U.S. Pat. No. 3,943,981, issued Mar. 16, 1976 to De Brabander which teach a raised pile of loops. Related teachings are shown in U.S. Pat. No. 4,216,257, issued Aug. 5, 1980 to Schams et al., U.S. Pat. No. 4,454,183, issued Jun. 12, 1984 to Wollman and U.S. Pat. No. 4,463,486, issued Aug. 7, 1984 to Matsuda. These references teach heating the ends of polymeric monofilaments. Other related teachings of fastening systems produced by the first method are disclosed in U.S. Pat. No. 4,307,493, issued Dec. 29, 1981 to Ochiai and U.S. Pat. No. 4,330,907, issued May 25, 1982 to Ochiai.

The second general method commonly utilized to manufacture mechanical fastening systems is to mold or extrude the systems as illustrated in U.S. Pat. No. 3,147,528, issued Sep. 8, 1964 to Erb and U.S. Pat. No. 3,594,863, issued Jul. 27, 1971 to Erb. Continuous injection molding is taught in U.S. Pat. No. 3,594,865, issued Jul. 27, 1971 to Erb.

Various prong structures are illustrated in the prior art. For example, the references discussed above teach fastening systems having stems of generally constant cross section. U.S. Pat. No. 3,708,833, issued Jan. 9, 1973 to Ribich et al. discloses a prong which is somewhat tapered from the proximal end to the distal end and perpendicularly projects from the substrate.

European Patent Application No. 0,276,970, filed Jan. 26, 1988, by the Procter & Gamble Company in the name of Scripps discloses a fastening device having a constant cross section stem oriented at an angle between about 30° and about 90° relative to the base.

The prior art does not show methods of manufacture which produce free formed prongs. The prior art also does not show the structure of a mechanical fastening system wherein the prong is nonperpendicularly oriented relative to the substrate and has tapered sides. The prior art also does not show methods of manufacture which produce free formed prongs oriented substantially in the cross-machine direction of the substrate.

It is an object of this invention to provide a free formed mechanical fastening system produced by a method of manufacture similar to gravure printing. It is also an object of this invention to provide a fastening system having tapered prongs which do not perpendicularly project from the associated substrate. It is a further object of this invention to provide a fastening system having free formed prongs which are oriented substantially in the cross-machine direction of the substrate.

BRIEF SUMMARY OF THE INVENTION

The invention comprises a fastening system for attaching to a complementary receiving surface. The fastening system has a substrate and at least one free formed prong comprising a base, shank and engaging means. The base of the prong is joined to the substrate and the shank is contiguous with and projects outwardly from the base. The engaging means is joined to the shank and projects laterally beyond the periphery of the shank. The shank is nonperpendicularly oriented relative to the plane of the substrate. The shank has a leading edge and a trailing edge defining a leading angle and trailing angle respectively. The leading angle and trailing angle are substantially different from each other, so that the sides of the shank are nonparallel. The shank also has an azimuthal angle. The azimuthal angle can be between about 1° and about 180°, preferably between about 20° to about 160°, relative to the MD.

The fastening system may be made according to the process comprising the steps of heating a thermally sensitive material sufficiently to reduce its viscosity for processing, and preferably to at least its melting point. A means to deposit discrete amounts of the heated material is provided. The substrate to which the material is to be joined is transported in a first direction relative to the means for depositing the material. The material is deposited on the transported substrate in discrete amounts. The discrete amounts of material are then stretched in a direction having a vector component generally parallel to the plane of the substrate. The stretched material is severed to form a distal end and engaging means, and an azimuthal angle between about 1° to about 180°, preferably between about 20° to about 160°, is imparted to the shank.

An illustrative and suitable, but nonlimiting, use for the fastening system produced by the process of the present invention is in conjunction with a disposable absorbent garment, such as a diaper. This example of one usage of the present invention is more fully described below.

BRIEF DESCRIPTION OF THE DRAWINGS

While the Specification concludes with claims particularly pointing out and distinctly claiming the invention, it is believed the invention will be better understood from the following description taken in conjunction with the associated drawings in which like elements are described by the same reference numeral and related elements are designated by adding one or more prime symbols or incrementing the numeral by 100:

DETAILED DESCRIPTION OF THE INVENTION

Figure 1:
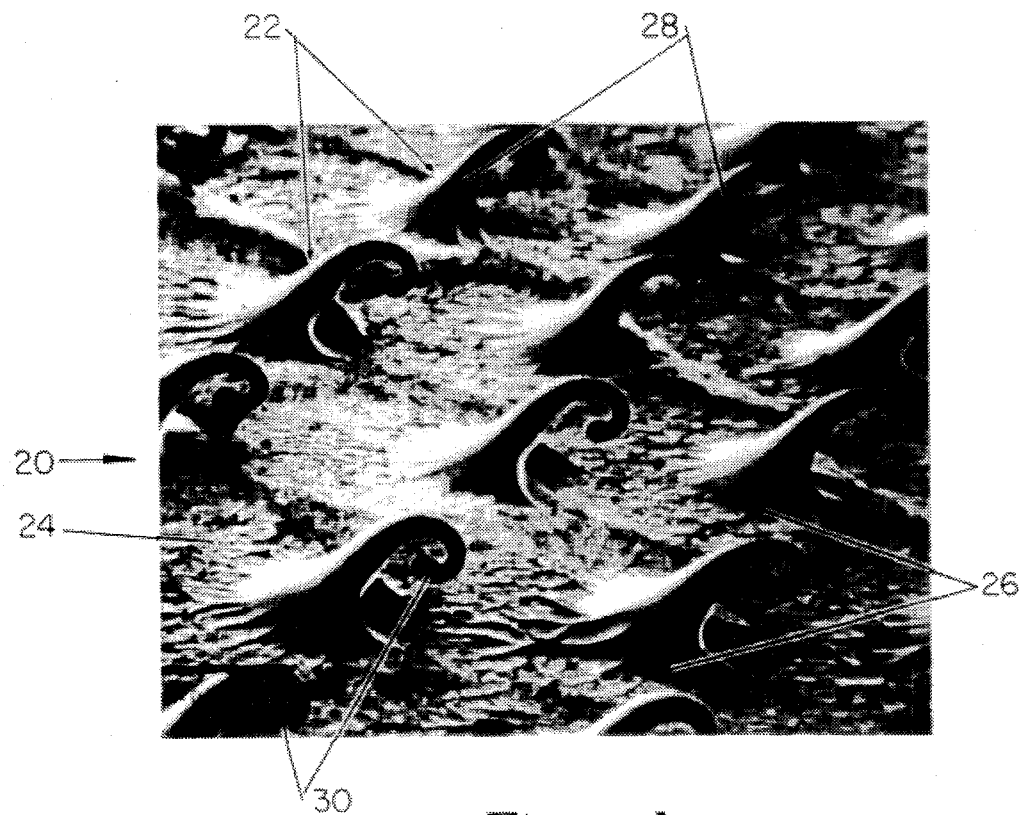
FIG. 1 is a perspective view of a fastening system of the present invention wherein the engaging means are oriented in substantially the same direction.

The fastening system 20 of the present invention comprises at least one prong 22, and preferably an array of prongs 22, joined to a substrate 24 in a predetermined pattern as shown in FIG. 1. The prongs 22 have a base 26, shank 28 and engaging means 30. The bases 26 of the prongs 22 contact and adhere to the substrate 24, and support the proximal ends of the shanks 28. The shanks 28 project outwardly from the substrate 24 and bases 26. The shanks 28 terminate at a distal end which is joined to an engaging means 30. The engaging means 30 radially project laterally from the shanks 28 in one or more directions and may resemble a hook-shaped tine. As used herein, the term "lateral" means having a vector component generally parallel to the plane of the substrate 24 at the principal prong 22 under consideration. The projection of an engaging means 30 from the shank 28 periphery in a lateral direction allows the engaging means 30 to be secured to a complementary receiving surface (not shown). The engaging means 30 is joined to, and preferably contiguous with, the distal end of the prong 22. It will be apparent the engaging means 30 may be joined to the prong 22 at a position between the base 26 and the distal end of the shank 28.

The array of prongs 22 may be produced by any suitable method, including methods which yield a free formed prong 22 as described and claimed hereinbelow. As used herein, the term "free formed" means a structure which is not removed from a mold cavity or extrusion die in solid form or with a defined shape. The prongs 22 are deposited onto a noncontiguous substrate 24 in a molten, preferably liquid state and solidify, by cooling until rigid and preferably freezing, into the desired structure and shape as described hereinafter.

Figure 4:
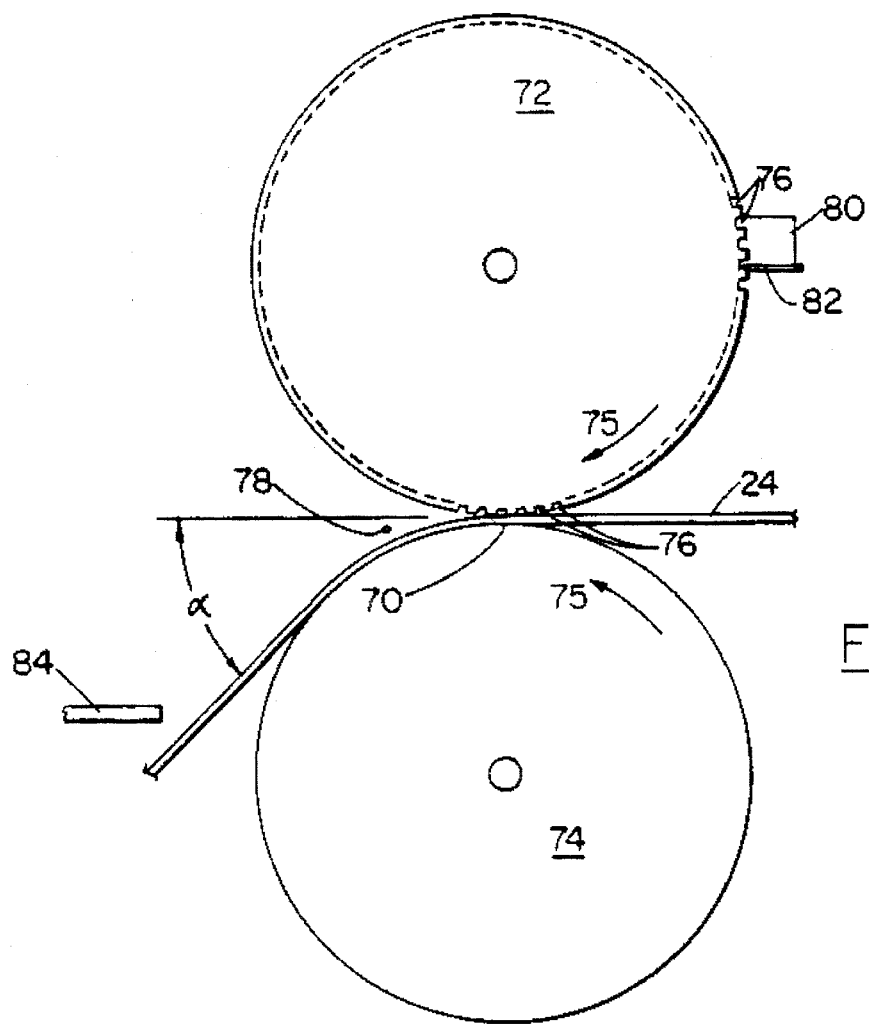
FIG. 4 is a side elevational schematic view of one apparatus which can be used to produce the fastening system of the present invention.

The free formed array of prongs 22 is preferably produced by a manufacturing process which is similar to that process commonly known as gravure printing. Using this process, a substrate 24 having opposed faces is passed between the nip 70 of two generally cylindrical rolls, a print roll 72 and a backing roll 74, as illustrated at FIG. 4. The rolls 72 and 74 have generally parallel centerlines and are maintained in contacting relationship with the substrate 24 as it passes through the nip 70. One of the rolls, referred to as the print roll 72, has an array of blind, closed-end cavities, referred to as cells 76, corresponding to the desired pattern of prongs 22 to be deposited on the substrate 24. The second roll, referred to as the backing roll 74, provides the reaction against the print roll 72 to position the substrate 24 against the print roll 72 as the substrate 24 passes through the nip 70. Liquid, thermally sensitive material, preferably thermoplastic material, from which the prongs 22 are to be formed is supplied from a heated source, such as a trough 80. The thermally sensitive material is introduced into the cells 76 as the print roll 72 is rotated about its centerline. The cells 76 containing the thermally sensitive material transport it until contact with the substrate 24 is made and deposit this material onto the substrate 24 in the desired pattern.

As relative displacement between the substrate 24 and rolls 72 and 74 continues, the prongs 22 are stretched with a lateral component, generally parallel to the plane of the substrate 24, forming the shank 28 and the engaging means 30. Finally, the moil of the prong 22 is severed from the engaging means 30 by a severing means 78. Due to the viscoelastic properties of the thermoplastic, the prong 22 contracts. It is also believed that the prong 22 retracts under the influences of gravity and shrinkage which occur during cooling. The prong 22 then cools, and preferably freezes, into a solid structure having the engaging means 30 contiguous with the shank 28.

The fastening system 20 is secured to a complementary receiving surface. As used herein, the term "receiving surface" to which the engaging means 30 of the fastening system 20 are secured refers to any plane or surface having an exposed face with tightly spaced openings complementary to the engaging means 30 and defined by one or more strands or fibers or, alternatively, which exposed face is capable of localized elastic deformation so that the engaging means 30 may become entrapped and not withdrawn without interference. The openings or localized elastic deformations allow for entry of the engaging means 30 into the plane of the receiving surface, while the strands (or nondeformed material) of the receiving surface interposed between the openings (or deformed areas) prevent withdrawal or release of the fastening system 20 until desired by the user or either the peel or shear strength of the fastening system 20 is otherwise exceeded. The plane of the receiving surface may be flat or curved.

A receiving surface having strands or fibers, is said to be "complementary" if the openings between strands or fibers are sized to allow at least one engaging means 30 to penetrate into the plane of the receiving surface, and the strands are sized to be engaged or intercepted by the engaging means 30. A receiving surface which is locally deformable is said to be "complementary" if at least one engaging means 30 is able to cause a localized disturbance to the plane of the receiving surface, which disturbance resists removal or separation of the fastening system 20 from the receiving surface.

Suitable receiving surfaces include reticulated foams, knitted fabrics, nonwoven materials, and stitchbonded loop materials, such as Velcro brand loop materials sold by Velcro USA of Manchester, N.H. A particularly suitable receiving surface is stitchbonded fabric Number 970026 sold by the Milliken Company of Spartanburg, S.C.

Referring back to FIG. 2 to examine the components of the fastening system 20 in more detail, the substrate 24 of the fastening system 20 should be strong enough to preclude tearing and separation between individual prongs 22 of the fastening system 20, be a surface to which the prongs 22 will readily adhere and be capable of being joined to an article to be secured as desired by a user. As used herein the term "join" refers to the condition where a first member, or component, is affixed, or connected to a second member or component, either directly; or indirectly, where the first member or component is affixed or connected to an intermediate member, or component which in turn is affixed, or connected, to the second member or component. The association between the first member, or component, and the second member, or component, is intended to remain for the life of the article. The "substrate" is any exposed surface to which one or more prongs 22 are joined.

The substrate 24 should also be capable of being rolled, to support conventional manufacturing processes, flexible so that the substrate 24 may be bent or flexed in a desired configuration, and able to withstand the heat of the liquid prongs 22 being deposited thereon without melting or incurring deleterious effects until such prongs 22 freeze. The substrate 24 should also be available in a variety of widths. Suitable substrates 24 include knitted fabric, woven materials, nonwoven materials, rubber, vinyl, films, particularly polyolefinic films and preferably kraft paper. White kraft paper having a basis weight of 0.08 kilograms per square meter (50 pounds per 3,000 square feet) has been found suitable.

The base 26 is the generally planar portion of the prong 22 which is attached to the substrate 24 and is contiguous with the proximal end of the shank 28 of the prong. As used herein, the term "base" refers to that portion of the prong 22 which is in direct contact with the substrate 24 and supports the shank 28 of the prong 22. It is not necessary that a demarcation be apparent between the base 26 and the shank 28. It is only important that the shank 28 not separate from the base 26 and that the base 26 not separate from the substrate 24 during use. The base 26 cross section should provide sufficient structural integrity, and hence area, for the desired peel and shear strengths of the fastening system 20, based on the density of the pattern of prongs 22 and length of the shanks 28 of the individual prongs 22 and further provide adequate adhesion to the substrate 24. If a longer shank 28 is utilized, the base 26 should generally be of greater cross sectional area to provide sufficient adhesion to the substrate 24 and adequate structural integrity.

The shape of the footprint of the base 26 on the substrate 24 is not critical, and may be amplified in any direction to provide greater structural integrity and thus a greater peel strength in that direction. As used herein, the term "footprint" refers to the planar contact area of the base 26 on the substrate 24. The aspect ratio of the sides of the footprint should not be too great, otherwise the prong 22 may be unstable when subjected to forces parallel to the shorter side of the footprint. An aspect ratio of less than about 1.5:1 is preferred, and a generally circular footprint is more preferred.

For the embodiment described herein, a base 26 having a footprint of generally circular shape and approximately 0.76 millimeters to 1.27 millimeters (0.030 to 0.050 inches) in diameter is suitable. If it is desired to make the fastening system 20 have a greater peel or shear strength in a particular direction, the cross sectional area of the base 26 may be modified to amplify such direction, so that the strength and structural integrity relative to the axis orthogonal to such direction increases. This modification causes the prongs 22 to be stronger when pulled in the amplified direction of the base 26.

The shank 28 is contiguous with the base 26 and projects outwardly from the base 26 and substrate 24. As used herein, the term "shank" refers to that portion of the prong 22 which is intermediate of and contiguous with the base 26 and the engaging means 30. The shank 28 provides longitudinal spacing of the engaging means 30 from the substrate 24. As used herein, the term "longitudinal" means in a direction having a vector component away from the substrate 24, which direction increases the perpendicular distance to the plane of the substrate 24 at the base 26 of the prong 22, unless otherwise-specified to be a direction having a vector component towards such plane of the substrate 24.

Associated with the shank 28 and base 26 of each prong 22 is an origin 36. The "origin" of the shank 28 is the point which may be thought of as the center of the base 26, and is typically within the footprint of the base 26. The origin 36 is found by viewing the prong 22, from the side view. The "side view" is any direction radially towards the shank 28 and base 26 which is also parallel to the plane of the substrate 24. If the fastening system 20 is manufactured by the process described and claimed below, it is preferred, but not necessary, that the prong 22 be viewed in the machine and cross-machine directions, relative to the travel of the substrate 24 through the nip 70, when determining the origin 36.

The lateral distance between the remote edges of the base 26 footprint for the particular side view under consideration is found, and this distance is bisected, yielding the midpoint of the base 26 for such view. When bisecting the footprint of the base 26 for the particular side view under consideration, minor discontinuities (such as fillets or asperities incident to the attachment to substrate 24) are ignored. This point is the origin 36 of the shank 28.

The shank 28 makes an angle $\alpha$ with the plane of the substrate 24. As used herein, the term "plane of the substrate" refers to the flat, planar surface of the substrate 24 at the base 26 of the principal prong 22 under consideration. The angle $\alpha$ is determined as follows. The prong 22 is viewed in profile. The "profile view" of the prong 22 is one of two particular side views and found as follows. The prong 22 is visually inspected from the side views such that the direction having the maximum lateral projection 38 becomes apparent. The "lateral projection" is the distance taken laterally and parallel to the plane of the substrate 24 from the center of the base 26 in such view, i.e. the origin 36 of the shank 28, to the projection of the furthest laterally remote point on the prong 22 visible in such view when such point is longitudinally and perpendicularly projected downward to the plane of the substrate 24.

Figure 2:
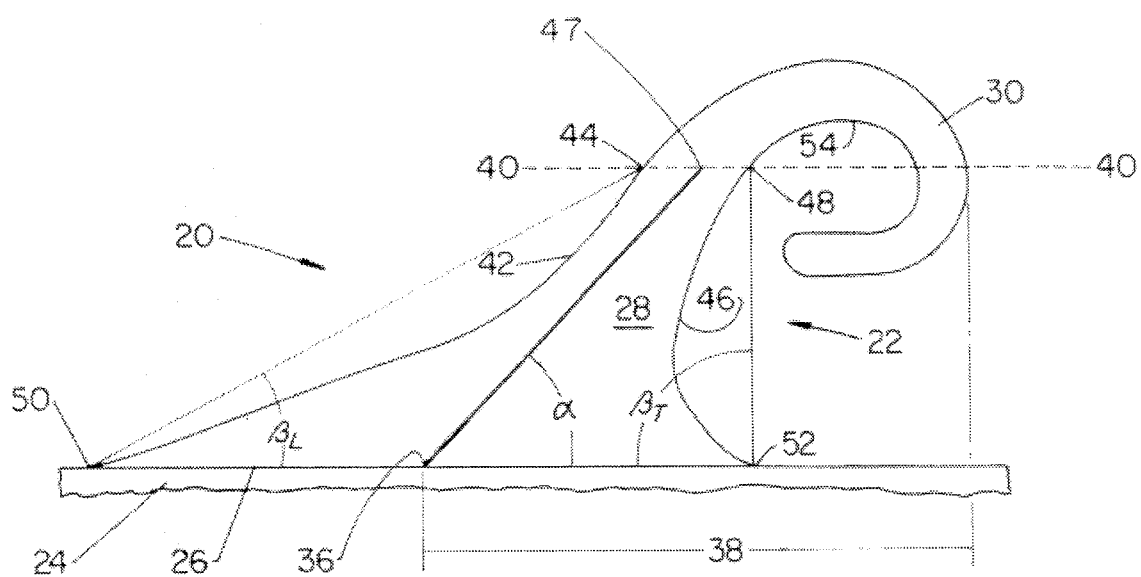
FIG. 2 is a side elevational view of one prong of the fastening system shown in FIG. 1.

It will be apparent to one skilled in the art that the maximum lateral projection 38 is that projection from the origin 36 to the outer periphery of the shank 28 or engaging means 30. The side view of the prong 22 which maximizes the lateral projection 38 is the profile view of such prong 22. It will also be apparent to one skilled in the art that if the fastening system 20 is produced by the process described and claimed below, and if the maximum lateral projection 38 is generally oriented in the machine direction, then the profile view will be generally oriented in the cross-machine direction. It will also be apparent that if the maximum lateral projection 38 is generally oriented in the cross-machine direction then the profile view will be generally oriented in the machine direction. The side elevational view shown in FIG. 2 is one of the profile views of the prong 22. It will be further apparent to one skilled in the art that there is another profile view, generally 180° opposite from the profile view shown (so that the maximum lateral projection 38 is oriented towards the left of the viewer). Either of the two profile views is generally equally well suited for the procedures and usages described hereinbelow.

The origin 36 of the shank 28 is found, as described above, with the prong 22 in the profile view. While still maintaining the prong 22 in the profile view, an imaginary cutting plane 40—40, generally parallel to the plane of the substrate 24, is then brought into tangency with the periphery of the prong 22 at the point or segment of the prong 22 having the greatest perpendicular distance from the plane of the substrate 24. This corresponds to the portion of the prong 22 having the highest elevation. The imaginary cutting plane 40—40 is then brought one-fourth of such greatest perpendicular distance closer to the substrate 24 from the point of highest elevation, so that the imaginary cutting plane 40—40 intercepts the prong 22 at a longitudinal elevation three-fourths of the perpendicular distance from the plane of the substrate 24.

The imaginary cutting plane 40—40 is then used to determine three points on the prong 22. The first point is that point where the cutting plane intercepts the leading edge 42 of the prong 22 and is referred to as the 75% leading point 44. The "leading edge" is the apex of the periphery of the shank 28 which longitudinally faces away from the plane of the substrate 24. The second point is disposed about 180° through the center of the prong 22 and is the point where the cutting plane 40—40 intercepts the trailing edge 46 of the prong 22 and is referred to as the 75% trailing point 48. The "trailing edge" is the apex of the periphery of the shank 28 which longitudinally faces towards the substrate 24 and is generally oppositely disposed from the leading edge 42. The straight line connecting these two points falls, of course, within the cutting plane 40—40 and is bisected to yield the midpoint 47 of the imaginary cutting plane 40—40. A straight line is then drawn connecting the midpoint 47 of the imaginary cutting plane 40—40 with the origin 36 of the shank 28 at the base 26. The included angle $\alpha$ this line defines relative to the plane of the substrate 24 is the angle $\alpha$ of the shank 28.

Alternatively stated, the angle $\alpha$ which the shank 28 makes relative to the plane of the substrate 24 is the 90° complement of that angle furthest from the perpendicular defined by the line, found in any side view, connecting the cutting plane midpoint 47 and the origin 36. Hence, the smallest angle relative to the plane of the substrate 24 when this line is viewed in any direction radially towards the shank 28, and particularly the origin 36, which direction is generally parallel to the plane of the substrate 24 and orthogonal to the perpendicular is the angle $\alpha$ of the shank 28. It is to be recognized that when a prong 22 having a maximum lateral projection 38 oriented in the machine direction is viewed approximately in the machine direction, or approximately 180° therefrom, or when a prong 22 having a maximum lateral projection 38 oriented in the cross-machine direction is viewed approximately in the cross-machine direction, the apparent angle $\alpha$ of the shank 28 will be about 90°. However, as discussed above, the angle $\alpha$ to be measured is that which deviates furthest from the perpendicular and, therefore, is generally that angle $\alpha$ determined when the prong 22 is viewed in profile, typically from about the cross-machine direction for a prong 22 oriented in the machine direction, and from about the machine direction for a prong 22 oriented in the cross-machine direction.

The angle $\alpha$ of the shank 28 may be generally perpendicular to the plane of the substrate 24, or is preferably oriented in an acute angular relation relative thereto to provide increased peel strength in a particular direction, which direction is generally parallel to the maximum longitudinal projection 38. However, the angle $\alpha$ of the shank 28 should not deviate excessively from the perpendicular, otherwise a fastening system 20 of more directionally specific shear strength results. For the embodiment described herein, a shank 28 having an angle $\alpha$ between about 45° and about 80°, preferably about 65°, works well. If the angle of the shank 28 is less than about 80°, the shank 28 is considered to be nonperpendicularly oriented relative to the plane of the substrate 24 (without regard to lateral orientation).

The imaginary cutting plane 40—40 and profile view can also be utilized to determine the angles of the leading edge 42 and the trailing edge 46 relative to the plane of the substrate 24. To determine these angles, the 75% leading point 44 and 75% trailing point 48 are found as described above. The base 26 leading point 50 is found as follows. The line through the base 26 as viewed in profile is brought to intersect the leading edge 42 of the shank 28. This intersection is the "base leading point." As noted above, minor discontinuities in the shank 28 near the base 26, incident to attachment to the substrate 24, are not considered when determining the base leading point 50. The 75% leading edge 42 point is connected by a straight line to the base leading edge 42 point. This straight line forms an included angle $\beta_L$ relative to the plane of the substrate 24 and opening in the direction of the origin 36 and center of the shank 28. The angle $\beta_L$ is referred to as the angle of the leading edge 42 or simply the leading edge angle.

The base trailing point 52 is generally disposed 180° from the base leading point 50, through the center of the base 26, and found as follows. The line through the footprint of the base 26 as viewed in profile is brought to intersect the trailing edge 46 of the shank 28. This intersection is the "base trailing point." As noted above, minor discontinuities in the shank 28 near the base 26, incident to attachment to the substrate 24, are not considered when determining the base trailing point 52. As described above, the 75% trailing point 48 is connected with the base trailing point 52 by a straight line. This straight line forms an included angle $\beta_T$ relative to the plane of the substrate 24 and opening in the direction of the origin 36 and center of the shank 28. The included angle $\beta_T$ is referred to as the angle of the trailing edge 46 or simply the trailing edge angle.

The leading edge 42 and trailing edge 46 included angles $\beta_L$ and $\beta_T$ define the parallelism of the sides of the shank 28. If the angles $\beta_L$ and $\beta_T$ of the leading and trailing edges 42 and 46 are not supplementary to each other (do not add to an arithmetic sum of about 180°) the sides of the shank 28 are said to be nonparallel. If the sides of the shank 28 are nonparallel, the straight lines which define the angles $\beta_L$ and $\beta_T$ (connecting the base leading and trailing points 50 and 52 with the 75% leading and trailing points 44 and 48 respectively) intersect, either above or below the plane of the substrate 24. If the angles $\beta_L$ and $\beta_T$ of the leading and trailing edges 42 and 46 are unequal and the lines defining such angles intersect above the plane of the substrate 24 (longitudinally outwardly of the base 26), the prong 22 will converge from the base 26 towards the distal end and engaging means 30. Only if the angles $\beta_L$ and $\beta_T$ of the leading and trailing edges 42 and 46 have the same sense i.e., are oriented in the same direction, and supplementary magnitudes are the angles $\beta_L$ and $\beta_T$ of the leading and trailing edges 42 and 46 determined to be equal and the sides of the shank 28 to be parallel.

A shank 28 having a leading edge 42 which forms a leading edge angle $\beta_L$ with the substrate of about 45°±30° is suitable. A trailing edge 46 which forms a trailing edge angle $\beta_T$ with the substrate of about 65°±30° is suitable. A shank 28 having these angles $\beta_L$ and $\beta_T$ of the leading and trailing edges 42 and 46 works well with the aforementioned spectrum of included angles α of the shank 28 to yield a tapered shank 28, advantageously oriented relative to the substrate 24 to provide high shear and peel strengths without requiring excessive prong material.

The foregoing measurements are easily made using a Model 100-00 115 goniometer sold by Rame'-Hart, Inc. of Mountain Lakes, N.J. If more precise measurement is desired, it will be recognized by one skilled in the art that determination of the profile view, origin 36, cutting plane 40—40, leading angle $\beta_L$, trailing angle $\beta_T$, base points 50 and 52, 75% points 44 and 48, and the angle α of the shank 28 can be advantageously performed by making a photograph of the prong 22. A model 1700 scanning electron microscope sold by Amray, Inc. of New Bedford, Mass. has been found to work well for this purpose. If necessary, several photographs may be taken to determine the maximum lateral projection 38 and hence, either profile view.

The shank 28 should longitudinally project from the base 26 a distance sufficient to space the engaging means 30 from the substrate 24 at an elevation which allows the engaging means 30 to readily intercept or engage the strands of the receiving surface. A relatively longer shank 28 provides the advantage that it can penetrate deeper into the receiving surface and thereby allow the engaging means 30 to intercept or engage a greater number of strands or fibers. Conversely, a relatively shorter shank 28 length provides the advantage that a relatively stronger prong 22 results, but also provides correspondingly less penetration into the receiving surface and may therefore be unsuitable for receiving surfaces such as wool or loosely stitched bonded materials which have less densely packed strands or fibers.

If a knitted or woven material receiving surface is utilized, a relatively shorter shank 28 having a longitudinal length from the substrate 24 to the point or segment of highest elevation of about 0.5 millimeters (0.020 inches), preferably at least about 0.7 millimeters (0.028 inches), is suitable. If a high loft material receiving surface having a caliper greater than about 0.9 millimeters (0.035 inches) is utilized, a relatively longer shank 28 having a greater longitudinal dimension of at least about 1.2 millimeters (0.047 inches), preferably at least about 2.0 millimeters (0.079 inches), is more suitable. As the shank 28 length increases, and shear strength correspondingly diminishes, the density of the prongs 22 of the fastening system 20 may be increased to compensate for such loss of shear strength.

As described above, the longitudinal length of the shank 28 determines the longitudinal spacing of the engaging means 30 from the substrate 24. The "longitudinal spacing" is the least perpendicular distance from the plane of the substrate 24 to the periphery of the engaging means 30. For an engaging means 30 of constant geometry, the longitudinal spacing of the engaging means 30 from the substrate 24 becomes greater with increasing longitudinal shank 28 length. A longitudinal spacing of at least about twice the strand or fiber diameter of the intended receiving surface, and preferably about 10 times as great as such fiber or strand diameter provides good interception or engagement and retention of such strands or fibers by the engaging means 30 of the fastening system 20. For the embodiment described herein, a prong 20 having a longitudinal spacing of about 0.2 millimeters to about 0.8 millimeters (0.008 to 0.03 inches) works well.

The shape of the cross section of the shank 28 is not critical. Thus the shank 28 may be of any cross section desired, according to the aforementioned parameters relating to the cross section of the base 26. The "cross section" is the planar area of any part of the prong 22 taken perpendicular to the shank 28 or the engaging means 30. As noted above, the shank 28 is preferably tapered to decrease in cross section as the distal end of the shank 28 and engaging means 30 of the prong 22 are longitudinally and laterally approximated. This arrangement provides a corresponding decrease in the moment of inertia of the shank 28 and engaging means 30 resulting in a prong 22 of more nearly constant stress when separation forces are applied to the fastening system 20, and thereby diminishes the quantity of superfluous materials incorporated into the prong 22.

To maintain the desired geometry over a wide range of prong 22 sizes, a generally uniform ratio of cross sectional areas can be utilized to scale the prongs 22. One ratio which generally controls the overall taper of the prong 22 is the ratio of the area of the cross section of the base 26 to the area of the cross section of the prong 22, at the highest elevation of the prong 22. The phrase "highest elevation" refers to the that point or segment of the shank 28 or the engaging means 30 having the greatest perpendicular distance from the plane of the substrate 24. Typically, prongs 22 having a base 26 cross sectional area to highest elevation cross sectional area ratio in the range of about 4:1 to about 9:1 work well.

A generally circular shank 28 which tapers from a base 26 diameter, as discussed above, ranging from about 0.76 millimeters to about 1.27 millimeters (0.030 to about 0.050 inches) to a highest elevation diameter, of about 0.41 millimeters to about 0.51 millimeters (0.016 to 0.020 inches) has been found suitable for the embodiment discussed herein. Specifically, a generally circular shaped cross section of about 0.46 millimeters (0.018 inches) diameter at the highest elevation provides a cross sectional area at highest elevation of about 0.17 square millimeters (0.0003 square inches). A generally circular shaped base 26 cross section of about 1.0 millimeters (0.040 inches) provides a base 26 cross sectional area of about 0.81 square millimeters (0.0013 square inches). This structure results in a ratio of base 26 cross sectional area to highest elevation cross sectional area of about 5:1, which is within the aforementioned range.

The engaging means 30 is joined to the shank 28, and preferably is contiguous with the distal end of the shank 28. The engaging means 30 projects radially away and outwardly from the periphery of shank 28, and may further have a vector component which longitudinally projects, i.e. towards or away from the substrate 24. As used herein the term "engaging means" refers to any protrusion lateral to the periphery of shank 28 (other than minor asperities in the periphery of the shank 28), which protrusion resists separation or removal from a receiving surface. The term "periphery" means the outer surface of the prong 22. The term "radially" means from or towards the perpendicular to the substrate 24, which perpendicular passes through the origin 36 which is generally centered within the footprint of the base 26.

Particularly, the lateral protrusion has a vector component parallel to and facing towards the plane of the substrate 24. It is to be recognized that the engaging means 30 and shank 28 may have both lateral and longitudinal vector components. It is not important that a sharply defined terminus of the shank 28 distal end be apparent, or that a demarcation between the shank 28 and engaging means 30 be discernible at all. It is only necessary that a longitudinally oriented face of the shank 28 periphery be interrupted so that the engaging means 30 has a face with a vector component parallel to and facing the plane of the substrate The engaging means 30 may have a greater lateral projection 38 than the shank 28, or vice-versa, as desired. As illustrated in the figures, the engaging means 30 is preferably generally arcuate and may have a reentrant curve. If the engaging means 30 has a reentrant curve, the engaging means 30 includes a segment which longitudinally approximates the substrate 24 at the base 26 or a location laterally spaced from the base 26. This segment is laterally directed towards the shank 28, although the segment need not be radially directed towards the origin 36.

The engaging means 30 of each prong 22 of the fastening system 20 may laterally extend substantially in the same direction, if a relatively unidirectionally oriented peel strength is desired, or may be randomly oriented to provide substantially isotropic peel strengths in any lateral direction. The engaging means 30 may be hook-shaped tines which project substantially from one side of the shank 28, defining a generally convex outline, and penetrate the opening of the receiving surface to intercept the strands or fibers of the receiving surface at the inner radius of curvature 54 of the engaging means 30. The interference between the engaging means 30 and strands or fibers of the receiving surface prevents release of the fastening system 20 from the receiving surface until the peel strength or shear strength of the fastening system 20 is exceeded. The engaging means 30 should not radially project too far in the lateral direction, otherwise the engaging means 30 may not penetrate the opening of the receiving surface. The cross section of the engaging means 30 should be sized to penetrate the openings of the receiving surface. The cross sectional area and geometry of the engaging means 30 are not critical, so long as the engaging means 30 has structural integrity which provides sufficient shear and bending strengths to accommodate the desired peel and shear strengths of a fastening system 20 having an array of prongs 22 of a given density. For the embodiment described herein, a hook-shaped tine engaging means 30 having a maximum lateral projection 38 from the center of the base 26 to the remote lateral periphery of about 0.79 millimeters to about 0.90 millimeters (0.03 to 0.04 inches) is suitable.

The array of prongs 22 may be of any pattern and density as desired, to achieve the peel and shear strengths required for the particular application of the fastening system 20. Generally as the array density increases, peel strength and shear strength proportionately increase in a linear fashion. The individual prongs 22 should not be so closely spaced as to interfere with and prevent the engaging means 30 of the adjacent prongs 22 from intercepting strands or fibers of the receiving surface. If the prongs 22 are too closely spaced, compacting or matting of the receiving surface strands or fibers may occur, occluding the openings between the strands or fibers. Conversely, the prongs 22 should not be so distantly spaced as to require an excessive area of substrate 24 to provide a fastening system 20 of adequate shear and peel strengths.

It is advantageous to dispose the prongs 22 in rows, so that each prong 22 is generally equally spaced from the adjacent prong 22. The rows are generally oriented in the machine direction and cross-machine direction according to the manufacturing process described and claimed below. Generally, each machine direction and cross-machine direction row of prongs 22 should be equally spaced from the adjacent machine direction and cross-machine direction rows of prongs 22, to provide a generally uniform stress field throughout the fastening system 20 and the receiving surface when separation forces are applied to the fastening system 20 and the receiving surface.

As used herein the term "pitch" refers to the distance, measured either in the machine direction or cross-machine direction, between the centers of the footprints of the bases 26 of prongs 22 in adjacent rows. Typically a fastening system 20 having an array of prongs 22 with a pitch ranging from about 1.02 millimeters to about 5.08 millimeters (0.04 to 0.20 inches) in both directions is suitable, with a pitch of about 2.03 millimeters (0.08 inches) being preferred. Adjacent cross-machine direction rows are preferably offset approximately one-half pitch in the cross-machine direction to double the distance in the machine direction between the adjacent cross-machine direction rows.

The prongs 22 may be thought of as disposed in a matrix on a one square centimeter grid having an array of prongs 22 with about 2 to about 20 rows of prongs 22 per centimeter (5 to 50 rows per inch) in both the machine and cross-machine directions, preferably about 9 rows of prongs 22 per centimeter (23 rows per inch) in each direction. This grid will result in a fastening system 20 having about 4 to about 400 prongs per square centimeter (25 to 2500 prongs per square inch) of substrate 24.

The fastening system 20 prongs 22 may be made of any thermally sensitive material which is stable and shape retaining when solid, but not so brittle that failure occurs when the fastening system 20 is subjected to separation forces. As used herein, "thermally sensitive" means a material which gradually changes from the solid state to the liquid state upon the application of heat. Failure is considered to have occurred when the prong 22 has fractured or can no longer sustain a reaction in the presence of and when subjected to separation forces. Preferably the material has an elastic tensile modulus, measured according to ASTM Standard D-638, of about 24,600,000 to about 31,600,000 kilograms per square meter (35,00 to 45,000 pounds per square inch).

Further, the prong material should have a melting point low enough to provide for easy processing and a relatively high viscosity to provide a tacky and tough consistency at temperatures near the material melting point, so that the shanks 28 may be stretched and the engaging means 30 easily formed according to the method of manufacture recited below. It is also important that the prongs 22 be viscoelastic, to allow for more variation in the parameters affecting prong 22 structure, and particularly the geometry of the engaging means 30. Material having a complex viscosity ranging from about 20 to about 100 Pascal seconds at the temperature of application to the substrate 24 is suitable.

The viscosity may be measured with a Rheometrics Model 800 Mechanical Spectrometer using the dynamic operating mode at a 10 Hertz sampling frequency and 10% material strain. A disk and plate type geometry is preferred, particularly with a disk having a radius of about 12.5 millimeters and a gap of about 1.0 millimeters between the disk and plate.

The prongs 22 are preferentially comprised of a thermoplastic material. The term "thermoplastic" refers to uncrosslinked polymers of a thermally sensitive material which flows under the application of heat or pressure. Hot melt adhesive thermoplastics are particularly well suited to manufacture/the fastening system 20 of the present invention, particularly in accordance with the process described and claimed below. As used herein the phrase "hot melt adhesive" refers to thermoplastic compounds, normally solid at room temperature, which become fluid at elevated temperatures and which are applied in the molten state. Examples of hot melt adhesives may be found in the "Handbook Of Adhesives", Second Edition by Irving Skeist, published in 1977 by Van Nostrand Reinhold Company, 135 West 50th Street, New York, N.Y., 10020, which is incorporated herein by reference. Polyester and polyamide hot melt adhesives are particularly suitable and preferred. As used herein, the terms "polyester" and "polyamide" mean chains having repeating ester and amide units respectively.

If a polyester hot melt adhesive is selected, an adhesive having a complex viscosity of about 23±2 Pascal seconds at about 194° C. has been found to work well. If a polyamide hot melt adhesive is selected, an adhesive having a complex viscosity of about 90±10 Pascal seconds at about 204° C. has been found to work well. A polyester hot melt adhesive marketed by the Bostik Company of Riddleton, Mass. as No. 7199 has been found to work well. A polyamide hot melt adhesive marketed by the Henkel Company of Kankakee, Ill. under the tradename Macromelt 6300 has been found to work well.

Figure 3:
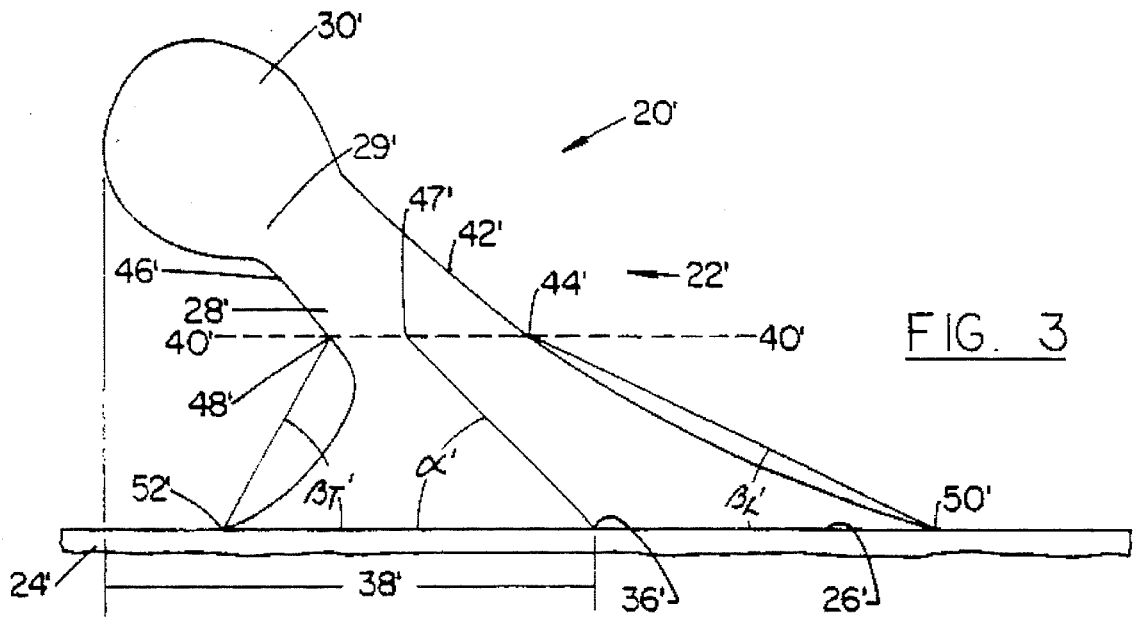
FIG. 3 is a side elevational view of a second embodiment having a generally semispherically shaped engaging means.

In a second embodiment of the fastening system 20', illustrated by FIG. 3, the engaging means 30' may be generally semispherically (mushroom) shaped. The term "semispherical" means a generally round shape, protruding in multiple directions and is inclusive of hemispheres and spheres, but not limited to regular shapes. This geometry, particularly the generally spherically shaped engaging means 30' structure, provides the advantage that less disturbance to the strands of the receiving surface typically occurs when the engaging means 30' is removed from the receiving surface. This causes less visible damage to the receiving surface, allowing it to be reused a greater number of times. If the semispherically shaped engaging means 30' is selected, the shank 28' is preferably more nearly orthogonal to the plane of the substrate 24', to allow easier penetration into the openings of the receiving surface and to reduce damage to the receiving surface as the engaging means 30' is released from the receiving surface. A shank 28' having an angle $\alpha'$ of about 70° to about 90° is suitable.

To provide a prong 22' of the proper proportions and having a generally semispherical engaging means 30', the engaging means 30' should radially protrude from the circumference of the shank 28' a lateral distance sufficient to intercept the strands of the receiving surface, but not protrude so far that the mass of the engaging means 30' is unable to be rigidly supported by the shank 28' or the shank 28' is otherwise unstable. As the angle $\alpha'$ of the shank 28' decreases, i.e. deviates further from the perpendicular, the mass of the engaging means 30' relative to the shank 28' structural integrity and cross sectional area becomes more critical.

A tapered shank 28', having the base 26' to highest elevation cross sectional area and diameter ratios described above, and an angle $\alpha'$ of the shank 28' of about 80° works well. It is to be recognized the highest elevation measurements are to be taken from the highest elevation of the shank 28' and not from the engaging means 30'.

For an embodiment, as illustrated in FIG. 3, which does not have a smooth transition from the shank 28' to the engaging means 30', and for which the demarcation between the shank 28' and engaging means 30' is easily determined, the imaginary cutting plane 40'—40' is three-fourths of the perpendicular distance from the plane of the substrate 24' to the plane tangent to the point of the engaging means 30' which is longitudinally closest to the plane of the substrate 24'. The cutting plane 40'—40' is then used to determine the angle $\alpha'$ of the shank 28', the leading edge angle $\beta_L'$ and trailing edge angle $\beta_T'$ as described above.

The engaging means 30' should radially project, in each lateral direction, from the periphery of the distal end 29' of the shank 28' at least about 25 percent of the diameter of the distal end 29' of the shank 28, and preferably at least about 38 percent of such diameter. Alternatively stated, if the diameter of the distal end 29' of shank 28' is normalized to 1.0, the diameter of the engaging means 30' should be at least 1.5, and preferably at least 1.75 times the diameter of the distal end 29' of the shank 28'. Furthermore, the diameter of the base 26' should be about 2.0 times the diameter of the distal end 29' of the shank 28'. The shank 28' height should be about 1.5 to about 2 times the diameter of the distal end 29' of the shank 28', to properly longitudinally space the engaging means 30' from the substrate 24'. The longitudinal dimension of the engaging means 30' may range from about 0.5 to about 1.5 times the diameter of the distal end 29' of the shank 28'.

The fastening system 20' of FIG. 3 is made by heating the engaging means 30 and distal end of the fastening system 20 of FIG. 2 to at least the melting point. This is accomplished by bringing the engaging means 30 and distal ends of the prongs 22 to a heat source longitudinally directed toward the plane of the substrate so that the base 26' and the proximal end of the shank 28' are not heated to at least the melting point. A suitable method is to bring the highest elevation of the prong to within about 3.3 millimeters to about 10.1 millimeters (0.1 to 0.4 inches) of a heat source, such as a hot wire heated to about 440° C.

The leading edge angle $\beta_L'$ and trailing edge angle $\beta_T'$ of the prong 22' will be similar to that of the corresponding hook-shaped tine style engaging means prong 22, from which the semispherically shaped engaging means style prong 22' was formed. This occurs because the angle $\alpha'$ of the shank 28' and leading edge and trailing edge angles $\beta_L'$ and $\beta_T'$ do not substantially change as the engaging means 30 of FIG. 2 is heated and melted to flow into the engaging means 30' of FIG. 3.

For the aforementioned Milliken 970026 receiving surface, the engaging means 30' of FIG. 3 should preferably have a lateral and longitudinal dimension of about 0.029 millimeters to about 0.032 millimeters (0.001 inches), and be disposed on a shank 28' having a base 26' diameter of about 0.30 millimeters to about 0.045 millimeters (0.012 to 0.002 inches) and a diameter at the distal end 29' of about 0.016 millimeters to about 0.020 millimeters (0.0006 to 0.0007 inches). The distal end 29' of the shank 28' should be disposed between about 0.44 millimeters and about 0.50 millimeters (0.017 inches to 0.020 inches) above the plane of the substrate 24', and the engaging means 30' should have a lateral projection 38' of about 0.56 millimeters to about 0.70 millimeters (0.022 to 0.028 inches), preferably about 0.64 millimeters (0.025 inches).

PROCESS OF MANUFACTURE

The fastening system 20 according to the present invention may be manufactured using a modified gravure printing process. Gravure printing is well known in the art as illustrated by U.S. Pat. No. 4,643,130 issued Feb. 17, 1988, to Sheath et al. and incorporated herein by reference to illustrate the general state of the art. Referring to FIG. 4, the substrate 24 is passed through the nip 70 formed between two rolls, a print roll 72 and a backing roll 74. The rolls 72 and 74 have substantially mutually parallel centerlines disposed generally parallel to the plane of the substrate 24. The rolls 72 and 74 are rotated about the respective centerlines and have generally equal surface velocities, in both magnitude and direction, at the nip point 70. If desired, both the print roll 72 and the backing roll 74 may be driven by an external motive force (not shown), or one roll driven by external motive force and the second roll driven by frictional engagement with the first roll. An alternating current electric motor having an output of about 1,500 watts provides adequate motive force. By rotating, the rolls 72 and 74 actuate a depositing means for depositing the prongs 22 onto the substrate 24.

The depositing means should be able to accommodate the temperature of the material of prongs 22 in the liquid state, provide substantially uniform pitch between the prongs 22 in both the machine and cross-machine directions and yield the desired density of prongs 22 within the array. Also, the depositing means should be able to produce prongs having various diameters of the base 26 and heights of the shank 23. The print roll 72, specifically, provides for the depositing means to deposit the prongs 22 on the substrate 24 in the desired array, discussed above, (or other pattern) according to the present manufacturing process. The phrase "depositing means" refers to anything which transfers liquid prong material from a bulk quantity to the substrate 24 in dosages corresponding to individual prongs 22. The term "deposit" means to transfer prong material from the bulk form and dose such material onto the substrate 24 in units corresponding to individual prongs 22.

One suitable depositing means for depositing prong material onto the substrate 24 is an array of one or more cells 76 in the print roll 72. As used herein the term "cell" refers to any cavity, or other component of the print roll 72, which transfers prong material from a source to the substrate 24 and deposits this material onto the substrate 24 in discrete units.

The cross sectional area of the cell 76, taken at the surface of the print roll 72, generally corresponds with the shape of the footprint of the base 26 of the prong 22. The cross section of the cell 76 should be approximately equal to the desired cross section of the base 26. The depth of the cell 76, in part, determines the longitudinal length of the prong 22, specifically the perpendicular distance from the base 26 to the point or segment of highest elevation. However, as the depth of the cell 76 increases to more than approximately 70 percent of the diameter of the cell 76, the longitudinal dimension of the prong 22 generally remains constant. This is because not all of the liquid prong material is pulled out of the cell 76 and deposited on the substrate 24. Due to the surface tension and viscosity of the liquid prong material, some of it will remain in the cell 76 and not be transferred to the substrate 24.

For the embodiment described herein, a blind, generally cylindrically shaped cell 76 having a depth between about 50 and about 70 percent of the diameter is adequate. If desired, the cell 76 may be somewhat frustoconically tapered in shape to accommodate conventional manufacturing processes, such as chemical etching.

If frustoconically shaped, the included angle of the taper of the cell 76 should be no more than about 45° to produce the preferred taper of the shank 28 and yield the base to highest elevation ratios discussed above. If the taper of the cell 76 has a greater included angle, a prong 22 having too much taper may result, If the included angle is too small, or the cell 76 is cylindrical, a shank 28 of generally uniform cross section may result, and thereby have areas of higher stress. For the embodiment described herein a cell 76 having an included angle of about 45°, a diameter at the roll periphery of about 0.89 millimeters to about 1.22 millimeters (0.035 to 0.048 inches) and a depth ranging from about 0.25 millimeters to about 0.51 millimeters) 0.01 to 0.02 inches produces a suitable prong 22.

The print roll 72 and backing roll 74 should be compressed, coincident with the line connecting the centerlines of the rolls, to press the adhesive from the cells 76 in the print roll 72 onto the substrate 24 and to provide sufficient frictional engagement to drive the opposing roll if it is not externally driven. The backing roll 74 should be somewhat softer and more compliant than the print roll 72 to provide cushioning of the prong material as it is deposited on the substrate 24 from the print roll 72. A backing roll 74 having a rubber coating with a Shore A durometer hardness of about 40 to about 60 is suitable. The rolls 72 and 74 may be pressed together with such a force that an impression in the machine direction of about 6.4 millimeters to about 12.7 millimeters (0.25 to 0.50 inches) is obtained. As used herein the term "impression" refers to the contact area of the softer roll on the substrate 24 as it passes through the nip 70.

The print roll 72 is preferably heated to prevent solidification of the prongs 22 during transfer from the source through the deposition on the substrate 24. Generally a print roll 72 surface temperature near the source material temperature is desired. A print roll 72 temperature of about 197° C. has been found to work well with the polyester hot melt adhesive marketed by the Bostik Company of Riddleton, Mass. as No. 7199.

It is to be recognized that a chill roll may be necessary if the substrate 24 is adversely affected by the heat transferred from the prong material. If a chill roll is desired, it may be incorporated into the backing roll 74 using means well known to one skilled in the art. This arrangement is often necessary if a polypropylene, polyethylene or other polyolefinic substrate 24 is used.

The material used to form the individual prongs 22 must be kept in a source which provides for the proper temperature to apply the prongs 22 to the substrate 24. Typically, a temperature slightly above the melting point of the material is desired. The material is considered to be at or above the "melting point" if the material is partially or wholly in the liquid state. If the source of the prong material is kept at too high a temperature, the prong material may not be viscous enough and may produce engaging means 30 which laterally connect to the prongs 22 adjacent in the machine direction. If the material temperature is very hot, the prong 22 will flow into a small, somewhat semispherically shaped puddle and an engaging means 30 will not be formed. Conversely, if the source temperature is too low, the prong material may not transfer from the source to the means for depositing the material or, subsequently, may not properly transfer from the depositing means 76 to the substrate 24 in the desired array or pattern. The source of the material should also impart a generally uniform cross-machine direction temperature profile to the material, be in communication with the means for depositing the adhesive material onto the substrate 24 and easily be replenished or restocked as the prong material becomes depleted.

A suitable source is a trough 80, substantially coextensive of that portion of the cross-machine dimension of the print roll 72 which has cells 76 and adjacent thereto. The trough 80 has a closed end bottom, an outboard side and ends. The top may be open or closed as desired. The inboard side of the trough 80 is open, allowing the liquid material therein to freely contact and communicate with the circumference of the print roll 72.

The source is externally heated by known means (not shown) to maintain the prong material in a liquid state and at the proper temperature. The preferred temperature is above the melting point but below that at which a significant loss of viscoelasticity occurs. If desired, the liquid material inside the trough 80 may be mixed or recirculated to promote homogeneity and an even temperature distribution.

Juxtaposed with the bottom of the trough 80 is a doctor blade 82 which controls the amount of prong material applied to the print roll 72. The doctor blade 82 and trough 80 are held stationary as the print roll 72 is rotated, allowing the doctor blade 82 to wipe the circumference of the roll 72 and scrape any prong material which is not disposed within the individual cells 76 from the roll 72 and allows such material to be recycled. This arrangement allows prong material to be deposited from the cells 76 to the substrate 24 in the desired array, according to the geometry of the cells 76 on the circumference of the print roll 72. As seen in FIG. 4, the doctor blade 82 is preferentially disposed in the horizontal plane, particularly the horizontal apex of the print roll 72, which apex is upstream of the nip point 70.

After being deposited onto the substrate 24, the prongs 22 are severed from the print roll 72 and the depositing means 76 by a severing means for severing 78 the prongs 22 into the engaging means 30 of the fastening system 20 and a moil. As used herein the term "moil" refers to any material severed from the prong 22 and which does not form part of the fastening system 20.

The severing means 78 should be adjustable to accommodate various sizes of prongs 22 and lateral projections 38 of engaging means 30 and also provide uniformity throughout the cross-machine direction of the array. The term "severing means" refers to anything which longitudinally separates the moil from the fastening system 20. The term "sever" refers to the act of dividing the moil from the fastening system 20 as described above. The severing means 78 should also be clean and should not rust, oxidize or impart corrodents and contaminates (such as moil material) to the prongs 22. A suitable severing means is a wire 78 disposed generally parallel to the axis of the rolls 72 and 74 and spaced from the substrate 24 a distance which is somewhat greater than the perpendicular distance from the highest elevation of the solidified prong 22 to the substrate 24.

Preferably the wire 78 is electrically heated to prevent build-up of the molten prong material on the severing means 78, accommodate any cooling of the prongs 22 which occurs between the time the prong material leaves the heated source and severing occurs and to promote lateral stretching of the engaging means 30. The heating of the severing means 78 should also provide for uniform temperature distribution in the cross-machine direction, so that an array of prongs 22 having substantially uniform geometry is produced.

Generally, as the prong material temperature increases a relatively cooler hot wire 78 temperature severing means can be accommodated. Also, as the speed of the substrate 24 is decreased, less frequent cooling of the hot wire 78 occurs as each prong 22 and moil are severed, making a relatively lower wattage hot wire 78 more feasible at the same temperatures. It should be recognized that as the temperature of the hot wire 78 is increased a prong 22 having a generally shorter shank 28 length will result. Conversely, the shank 28 length and lateral length of the engaging means 30 will be increased in inverse proportion as the temperature of the hot wire 78 is decreased. It is not necessary that the severing means 78 actually contact the prong 22 for severing to occur.

The prong 22 may be severed by the radiant heat emitted from the severing means 78.

For the embodiment described herein a round cross section nickel-chromium wire 78, having a diameter of about 0.51 millimeters (0.02 inches) heated to a temperature of about 343° C. to about 416° C. has been found suitable. It will be apparent that a knife, laser cutting or other severing means 78 may be substituted for the hot wire 78 described above.

It is important that the severing means 78 be disposed at a position which allows stretching of the prong material to occur prior to the prong 22 being severed from the moil. If the severing means 78 is disposed too far from the plane of the substrate 24, the prong material will pass underneath the severing means 78 and not be intercepted by it, forming a very long engaging means 30 which will not be properly spaced from the substrate 24 or adjacent prongs 22. Conversely, if the severing means 78 is disposed too close to the plane of the substrate 24, the severing means 78 will truncate the shank 28 and an engaging means 30 may not be formed.

A hot wire severing means 78 disposed approximately 14 millimeters to 22 millimeters (0.56 to 0.88 inches), preferably about 18 millimeters (0.72 inches) in the machine direction from the nip point 70, approximately 4.8 millimeters to 7.9 millimeters (0.19 to 0.31 inches), preferably about 6.4 millimeters (0.25 inches) radially outward from the backing roll 74 and approximately 1.5 millimeters to approximately 4.8 millimeters (0.06 to 0.19 inches), preferably about 3.3 millimeters (0.13 inches) radially outwardly from the print roll 72 is adequately positioned for the process of manufacture disclosed herein.

In operation, the substrate 24 is transported in a first direction relative to the depositing means 76. Rote particularly, the substrate 24 is transported through the nip 70, preferentially drawn by a take-up roll (not shown). This provides a clean area of substrate 24 for continuous deposition of prongs 22 and removes the portions of the substrate 24 having prongs 22 deposited thereon. The direction generally parallel to the principal direction of transport of the substrate 24 as it passes through the nip 70 is referred to as the "machine direction." The machine direction, as indicated by the arrow 75 of FIG. 4, is generally orthogonal the centerline of the print roll 72 and backing roll 74. The direction generally orthogonal to the machine direction and parallel to the plane of the substrate 24 is referred to as the "cross-machine direction."

The substrate 24 may be drawn through the nip 70 at a speed approximately 2% to approximately 10% greater than the surface speed of the rolls 72 and 74. This is done to minimize bunching or puckering of the substrate 24 near the means for severing 78 the prongs 22 from the means for depositing the prong material on the substrate 24. The substrate 24 is transported through the nip 70 in the first direction at about 3 to about 31 meters per minute (10 to 100 feet per minute).

The angle of the shank 28 can be influenced by the rate of transport of the substrate 24 past the nip 70. If prongs 22 having a shank angle α more nearly perpendicular to the substrate 24 is desired, a slower rate of transport of the substrate 24 in the first direction is selected. Conversely, if the rate of transport is increased, the angle α of the shank 28 decreases and an engaging means 30 have a greater lateral projection 38 will result.

If desired, the substrate 24 may be inclined at an angle γ, approximately 35° to approximately 55°, preferably about 45°, from the plane of the nip 70 towards the backing roll 74 to utilize the viscoelastic nature of the prong material and properly orient the engaging means 30 in the lateral direction, as well as longitudinal direction. This arrangement also provides a greater force to extract the prong material from the cell 76 and to pull the prong 22 away from the print roll 72. The angle γ from the plane of the nip 70 should be increased as a lesser angle α of the shank 28 is desired. Also, increasing the angle γ of deviation from the plane of the nip 70 has a weak, but positive effect to produce engaging means 30 having a greater lateral projection 38.

After depositing prong material from the cell 76 onto the substrate 24, the rolls 72 and 74 continue rotation, in the directions indicated by the arrows 75 of FIG. 4. This results in a period of relative displacement between the transported substrate 24 and the cells 76 during which period (prior to severing) the prong material bridges the substrate 24 and print roll 72. As relative displacement continues, the prong material is stretched until severing occurs and the prong 22 separated from the cell 76 of the print roll 72. As used herein the term "stretch" means to increase in linear dimension, at least a portion of which increase becomes substantially permanent for the life of the fastening system 20.

As discussed above, it is also necessary to sever the individual prongs 22 from the print roll 72 as part of the process which forms the engaging means 30. When severed, a prong 22 is longitudinally divided into two parts, a distal end and engaging means 30 which remain with the fastening system 20 and a moil (not shown) which remains with the print roll 72 and may be recycled, as desired. After the prongs 22 are severed from the moil, the fastening system 20 is allowed to freeze prior to contact of the prongs 22 with other objects. After solidification of the prongs 22, the substrate 24 may be wound into a roll for storage as desired.

A nonlimiting illustration of the process shows the prong material to be disposed in the trough 80 and heated by means commonly known to one skilled in the art, to a temperature somewhat above the melting point. If a polyester resin hot melt adhesive is selected, a material temperature of approximately 177°–193° C., preferably about 186° C. has been found suitable. If a polyamide resin is selected, a material temperature of approximately 193°–213° C., preferably about 200° C. has been found suitable. A one side bleached kraft paper substrate 24 about 0.008 to about 0.15 millimeters (0.003 to 0.006 inches) in thickness works well with hot melt adhesive prongs 22. The prongs 22 are joined to the bleached side of the kraft paper substrate 24.

For the illustrated operation described herein, print roll 72 having an array of about 5 cells 76 per centimeter (13 cells 76 per inch) in both the machine direction and cross-machine directions, yielding a grid of about 26 cells 76 per square centimeter (169 cells 76 per square inch), is suitable. This grid density may be advantageously used with a print roll 72 having a diameter of about 16 centimeters (6.3 inches), with cells 76 about 1 millimeter (0.045 inches) in diameter and about 0.8 millimeters (0.030 inches) deep. A backing roll 74 having a diameter of about 15.2 centimeters (6.0 inches) and vertically registered has been found to work well with the aforementioned print roll 72. The rate of transport of the substrate 24 is about 3.0 meters per minute (10 feet per minute).

A nickel-chromium hot wire 78 having a diameter of about 0.5 millimeters (0.02 inches) disposed approximately 18 millimeters (0.72 inches) from the nip point 70 in the machine direction, approximately 0.3 millimeters (0.13 inches) radially outwardly from the print roll 72 and approximately 6.4 millimeters (0.25 inches) radially outwardly from the backing roll 74 is heated to a temperature of about 382° C. The fastening system 20 produced by this operation is substantially similar to that illustrated by FIG. 1, which fastening system 20 may be advantageously incorporated into the illustrative article of use discussed below.

Without being bound by any particular theory, it is believed that the geometry of the engaging means 30 is governed by the elastic properties of the hot melt adhesive used to make the prong 22 and the difference in the temperature between the trailing edge 46 and the leading edge 42 of the prong 22. The trailing edge 46 of the prong 22 is shielded and insulated from the heat originating from the severing means 78. Conversely, the leading edge 42 is directly exposed to the heat of the severing means 78, which causes the leading edge 42 to solidify or freeze after the trailing edge 46. This causes elongation of the leading edge 42 and contraction of the trailing edge 46, relative to each other. As this temperature difference is increased, a relatively longer engaging means 30 is formed.

If desired, a fastening system 20 having relatively very small prongs 22 (not shown) may be made by forming a natural pattern from the print roll 72. As used herein, the term "natural pattern" refers to array of prongs 22 resulting from a print roll 72 which does not have cells 76 disposed thereon, but instead which utilizes the surface of the roll 72 as the depositing means 76. Thus, the pattern of prongs 22 is formed by the clearance between the doctor blade 82 and the print roll 72, and to a lesser extent by the surface finish of the print roll 72.

The doctor blade 82 should be adjusted to provide about a gap of about 0.03 millimeters to about 0.08 millimeters (0.001 to 0.003 inches) in radial clearance from the print roll 72. To form a natural pattern, the very small sized prongs 22 resulting from such a print roll 72 are advantageously utilized with a reticulated foam receiving surface that does not have strands and openings therebetween, but rather incurs localized elastic deformations which resist separation of the fastening system 20.

Figure 5:
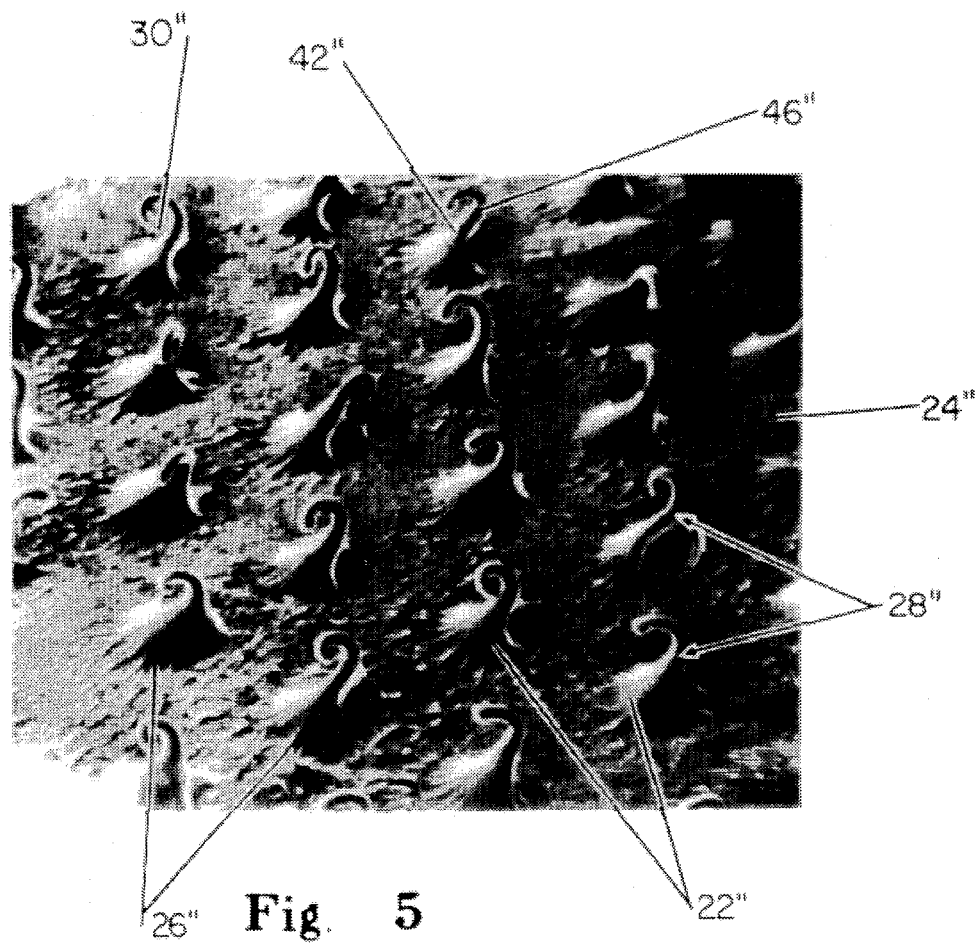
FIG. 5 is a perspective view of a fastening system of the present invention wherein the engaging means are oriented in substantially random directions.

Referring to FIG. 5, if a fastening system 20" of more nearly isotropic peel strength is desired, such a fastening system 20" may be formed by modifying the fastening system 20 of FIG. 1 through a second stage differential temperature process. As illustrated in FIG. 5, the fastening system 20 of FIG. 1 is further processed to provide shanks 28" with engaging means 30" which radially extend from the shanks 28" in various lateral directions of a generally random orientation. The phrase "random orientation" means having lateral projections 38" and profile views which significantly deviate in direction from those of the nearby prongs 22".

Without being bound by any particular theory, it is believed that this structure is accomplished by establishing a temperature differential between the profile surfaces or leading surfaces 42 and the trailing surfaces 46 of the prongs 22 of the fastening system 20 of FIG. 1, and that such temperature differential may be enhanced by radiation or preferably convection.

It is also believed that as a result of attaining a temperature differential of the leading surface 42" or the profile surfaces relative to the trailing surface 46", the engaging means 30" will substantially change or even reverse the orientation of lateral projection 38", providing a prong 22" which is oriented in a direction other than that which occurred when initially cooled or frozen. The differential temperature may be established by any source known to one skilled in the art, such as a heated wire or metal element, and preferably an air gun 84, disposed above the prongs 22" and capable of providing a directed temperature differential to the fastening system 20".

It is desired that the directed temperature differential source direct an air current towards the fastening system 20" within about ±90° of the first direction of substrate 24" travel, which is the machine direction. As used herein, the phrase "+90° of the first direction" means a direction having a vector component generally perpendicular to or generally counter to the first direction of travel of the substrate 24" and is inclusive of the direction generally opposite the first direction of travel.

If the directed temperature differential source 84 is disposed at an angle of about 180° relative to the first direction of travel of the substrate 24", the source 84 is directed towards the leading surfaces 42" of the prongs 22" of the fastening system 20", and generally opposite the machine direction of the process described and claimed herein. Directing the temperature differential of source 84 directly towards the leading surface 42" of a prong 22" will result in the lateral projection 38" of the engaging means 30" rotating, to change the orientation of the lateral projection about 180°. Prongs 22" disposed somewhat to the side, i.e. in the cross-machine direction, of the directed temperature differential source 84 will not have the engaging means 30" rotated about 180°, but instead engaging means 30" more nearly rotated about 90°. Thus, it is apparent that a directed temperature differential source 84 oriented in the cross-machine direction will provide a fastening system 20" having prongs 22" with various lateral orientations in the cross-machine direction according to the prong 22" position relative to the temperature differential source 84.

An air gun 84 discharging air at a temperature of about 88° C. at a distance of about 46 centimeters (18 inches) from the substrate 24" is a suitable differential temperature source. A 133-348 series heat gun sold by the Dayton Electric Manufacturing Company of Chicago, Ill. oriented at about 45° relative to the plane of the substrate 24" and disposed about 46 centimeters (18 inches) from the prongs produces a fastening system 20" pattern substantially similar to that shown in FIG. 5. It will be apparent to one skilled in the art that a one or more hot wires disposed above the prongs 22" and oriented in the machine direction will produce a fastening system 20" having cross machine directionally oriented engaging means 30" in a regular, somewhat striped pattern.

Without being bound by any theory, it is believed that the change in orientation of the engaging means 30" occurs due to the cooling of the profile surfaces or the leading surface 42" of the prong 22" relative to the trailing surface 46", which may occur if the temperature of the discharged air from the directed temperature source differential source 84 is less than the temperature of the periphery of such profile surfaces or leading surface 42". The temperature differential resulting from the cooling causes contraction of the portion of the prong 22" towards which the temperature differential source 84 is directed. This contraction may result in a change in the orientation of the engaging means 30" and lateral projection 38", due to the differential cooling of the leading surface 42" relative to the trailing surface 46". Without being bound by further theory, it is believed that relief of residual stresses which occur during cooling may influence the change in orientation of the lateral projection 38".

It will be further apparent to one skilled in the art that other variations are feasible. For example, a prong 22 having an engaging means 30 protruding in more than one direction may be formed or free formed prongs 22 may be produced by commonly known methods other than gravure printing. If desired, only one roll may be utilized in the manufacturing process, providing the substrate 24 contacts at least about 180' of the periphery of such roll.

It is frequently desirable to have a fastening system 20 of the present invention with the maximum lateral projection 38 of the prongs 22 oriented in a direction other than the machine direction. For example, when using the present invention as the fastening means of a disposable diaper, it is desirable that the maximum lateral projection 38 of the prongs 22 be oriented in a direction substantially perpendicular to the direction of travel of the disposable diaper on the manufacturing line. A diaper manufacturing line requires complex and expensive machinery to cut, reorient and apply the fastening system 20 if the maximum lateral projection 38 of the prongs 22 are oriented in the machine direction. A fastening system 20 of the present invention produced with the maximum lateral projection 38 of the prongs 22 oriented in the cross-machine direction, however, would not require re-orientation before being applied to a disposable diaper. It is therefore very advantageous to be able to manufacture the fastening system 20 of the present invention with the maximum lateral projection 38 of the prongs 22 oriented in a direction other than the machine direction.

Figure 7:
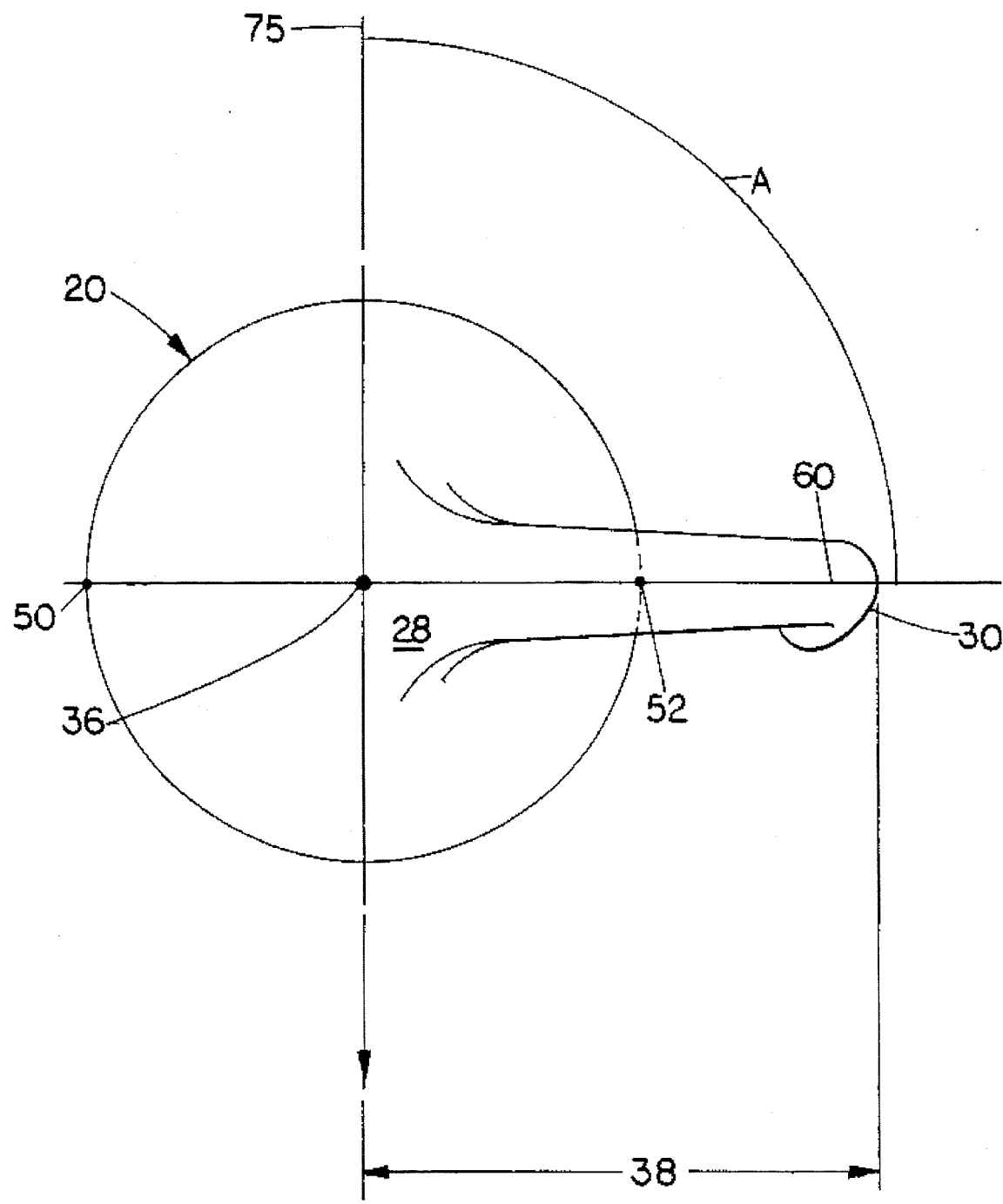
FIG. 7 is a top plan view of one prong having an azimuthal angle of about 90°.

There are two angles which are made by the shank 28 of prongs 22 produced by this process. The shank 28 makes an angle $\alpha$ with the plane of the substrate 24 as discussed hereinbefore, and the shank 28 also makes an azimuthal angle (indicated by a letter A, FIG. 7) relative to the machine direction of the substrate 24. As used herein, the term "azimuthal angle" refers to the angle the maximum lateral projection 38 makes relative to the machine direction of the substrate when viewed from above. As used herein "viewed from above" refers to viewing the prongs 22 from a direction which is perpendicular to the plane of the substrate 24. The term "machine direction" refers to the direction generally parallel to the principle direction of transport of the substrate 24 as it passes through the nip 70, and is indicated by an arrow 75 in FIG. 7. The azimuthal angle is measured by first determining the maximum lateral projection 38 of the prong 22 as disclosed hereinbefore. As shown in FIG. 7 the azimuthal angle, indicted by the letter A, is the angle relative to the machine direction which is made by a line 60 drawn parallel to the maximum lateral projection 38 when viewed from above. The azimuthal angle A can be measured relative to the machine direction in either the clockwise or counter-clockwise direction, but the azimuthal angle will not be greater than 180°. A fastening system 20 suitable for use on a disposable diaper, will preferably have prongs 22 with an azimuthal angle such that the maximum lateral projection 38 will be oriented in a direction having a vector component perpendicular to the machine direction of the substrate 24. Thus the prongs 22 may have an azimuthal angle greater than 0 degrees, between about 1 degrees and about 180 degrees, generally the azimuthal angle will be greater than about 20 degrees (20°–180°), greater than about 45 degrees (45°–180°), or greater than 60 degrees (60°–180°). The azimuthal angle of the prongs 22 made using the process described herein will preferably be from about 20 degrees to about 160 degrees, more preferably from about 45 degrees to about 135 degrees and most preferably from about 60 degrees to about 120 degrees. In a preferred embodiment shown in FIG. 7, the azimuthal angle of the prongs 22 will be about 90 degrees.

A method for imparting an azimuthal angle to the fastening system 20 is to bias the prongs 22 of the fastening system 20 while the prongs 22 are partially or wholly in a liquid state. As used herein the term "bias" refers to providing a force or influencing means in a direction having a vector component perpendicular to the machine direction of the substrate 24. The prongs 22 may be biased when they are newly formed and have not yet cooled and solidified and are still maleable, or the prongs 22 may be biased after they have cooled and solidified by reheating the prongs 22 so that they are maleable and will turn when biased. There are a number of methods available to bias the prongs 22 so as to impart an azimuthal angle.

Figure 8:
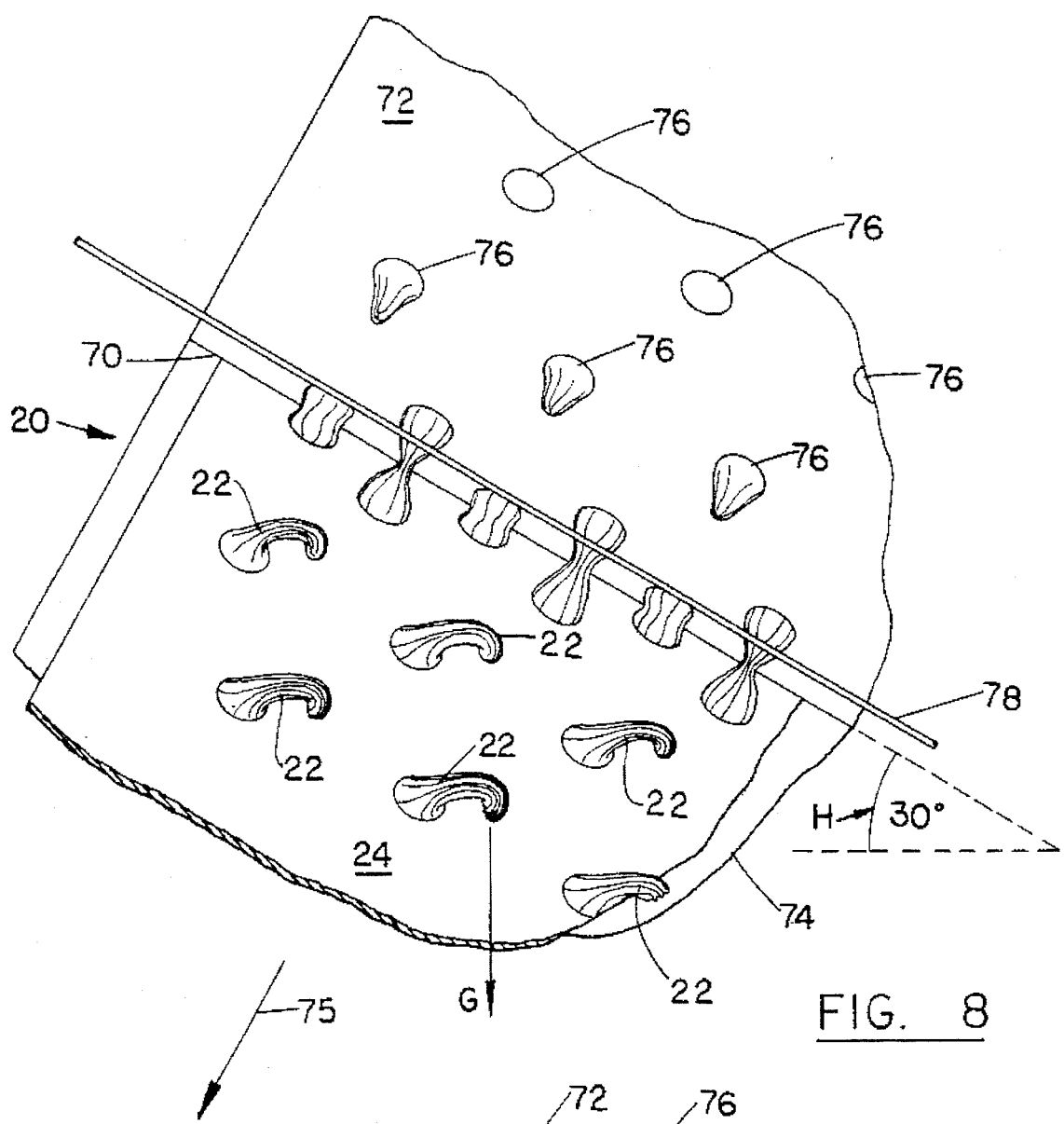
FIG. 8 is a front elevational view of one apparatus (only a portion of which is shown) which can be used to produce the fastening system of the present invention having azimuthally angled prongs.

A suitable method for imparting an azimuthal angle, is to bias the prongs 22 by causing gravitational forces to act upon the prongs 22 while the prongs 22 are partially or wholly in a liquid state such that the gravitational forces will pull the prongs 22 to the desired azimuthal angle. This can be accomplished by tilting the substrate 24 so that the plane of the substrate 24 when viewed in the machine direction, would not cut perpendicularly through a plum line, but rather would form an angle other than 90 degrees with a plum line. As the prongs 22 are printed and severed, the angle, indicated by the letter H in FIG. 8, of the substrate 24 relative to the horizontal allows gravitational forces to act upon the distal ends of the shanks 28 and engaging means 30 and pull the prongs 22 toward the longitudinal side of the substrate 24 having the lower altitude. Preferably, the print roll 72 and the backing roll 74 together are tilted or raised on one end from the horizontal, as shown in FIG. 8, so that as the substrate 24 passes through the nip 70 of the rolls the longitudinal edges of the substrate 24 will be at nonequal altitudes, and the gravitational forces, indicated by the letter G in FIG. 8, will act upon the prongs 22 to give the shank 28 an angle α with the substrate 24 and an azimuthal angle A (neither angle α or angle A are shown in FIG. 8). The substrate 24 should be tilted so that the plane of the substrate 24 forms an angle relative to the horizontal of at least about 15 degrees. Preferably the plane of the substrate 24 will be at an angle of at least 30 degrees.

In a nonlimiting example of the process, one may use Bostik polyester hot melt adhesive #7199 heated to a temperature of about 387° F. (197° C.); a print roll 72, having cells 76 with a diameter of 0.040 inches (0.102 centimeters) and a depth of 0.018 inches (0.046 centimeters), heated to a temperature of about 350° F. (177° C.); a substrate of white kraft paper having a basis weight of 0.08 milligrams per square meter traveling at a speed of 14 feet (4.266 meters) per minutes; and the print roll 72 and a backing roll 74 will be inclined to an angle of about 30° relative to the horizontal.

Another suitable method for imparting an azimuthal angle is to bias the prongs 22 by applying a pressure differential across the plane of the substrate 24 while the prongs 22 are partially or wholly in a liquid state such that the prongs are forced or drawn to the desired azimuthal angle. This may be accomplished by flowing a liquid or gas across the plane of the substrate 24 in a direction having a vector component perpendicular to the machine direction. The pressure differential will cause the prongs 22 to turn or reorient toward the side of the substrate having the lower pressure. Preferably, the pressure differential across the substrate 24 is achieved by creating a high pressure from one side of the substrate 24 using air jets, air needles or other means well known in the art. However, the pressure differential across the substrate 24 may also be achieved by producing a low pressure (i.e., vacuum or partial vacuum) from one side of the substrate 24, or by creating a high pressure from one side of the substrate 24 and at the same time creating a low pressure from the other side of the substrate 24. The side of the substrate 24 which represents the high pressure or low pressure side and the angle relative to the machine direction at which the fluid flows is dependent upon the azimuthal angle desired. The fluid medium used will preferably be air, though other gases and liquids may also be used. As used herein the term "high pressure" refers to a pressure greater than the ambient pressure of the air or other fluid which surrounds the prongs 22 as they are being azimuthally angled. As used herein the term "low pressure" refers to a pressure less than the ambient pressure of the air or other fluid which surrounds the prongs 22 as they are being azimuthally angled.

It should be understood that it would also be suitable to have the high pressure and/or low pressure originating from other than the sides of the substrate 24. That is, the high pressure source and/or low pressure source may be positioned such that the prongs 22 are forced and/or drawn in more than one direction, giving the fastening system 20 a more isotropic peel strength. As a nonlimiting example, a vacuum source may be disposed near the sides of the substrate 24 and a pressure source disposed near the middle of the substrate 24, such that the maximum lateral projection 38 of the prongs 22 will be influenced substantially away from the middle of the substrate 24 and toward the sides of the substrate 24.

When a pressure differential is used to impart an azimuthal angle to the prongs 22, frequently turbulence in the chosen fluid medium will cause some of the prongs 22 to scatter, or acquire an undesired azimuthal angle. To minimize the incidence of prongs 22 scattering, it is desirable to minimize the turbulent flow of the fluid medium and maintain a more streamline or laminar flow. There are a number of methods available to produce a substantially laminar flow.

Figure 9:
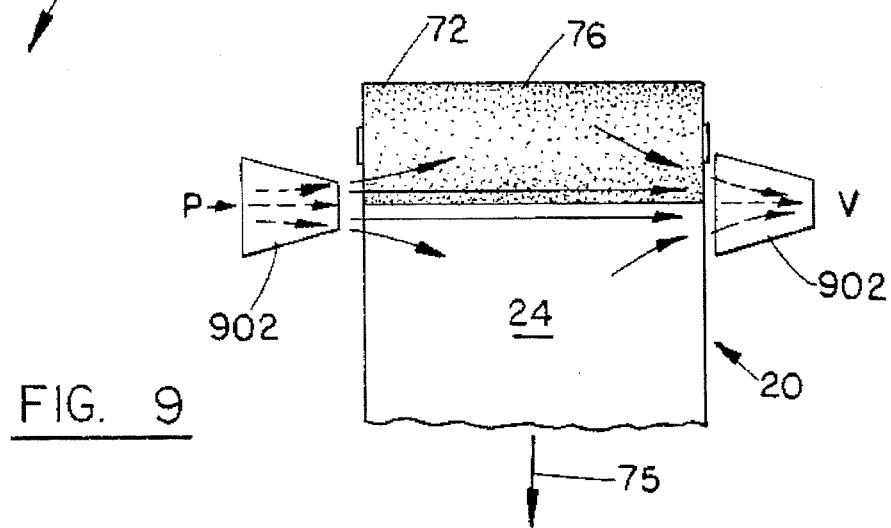
FIG. 9 is a top plan view of a second apparatus which can be used to produce the fastening system of the present invention having azimuthally angled prongs.

One method of producing a substantially laminar flow is through the use of one or more nozzles or flow amplifiers to impart controlled direction to a flow. As a non-limiting example, two commercial air flow amplifiers 902 will be used in tandem. The first air flow amplifier 902 (indicated by the letter P in FIG. 9) has the discharge flow of its outlet directed across the substrate 24. The second air flow amplifier 902 (indicated by the letter V in FIG. 9) has the suction of its inlet drawing from across the substrate 24. The discharge flow of the first air flow amplifier P is drawn into the inlet of the second air flow amplifier V creating a substantially linear air draft. The air flow amplifiers 902 are oriented relative to the substrate 24 to produce a low velocity linear air draft in a cross-machine direction. The preferred location of the linear air draft is immediately down stream of the cutting hot wire 78 (not shown in FIG. 9). Extraneous air current may be eliminated by the use of an enclosure (not shown) to surround the area where the linear air draft is applied. Suitable air flow amplifiers are commercially available from Vortec Corporation of Cincinnati, Ohio and marketed as Transvector Model 912/952, having a 25–100 SCFM rating. The required air pressure may vary, but about 1 psi to about 10 psi of air pressure works well.

Another suitable method for imparting an azimuthal angle to the prongs 22 is to bias the prongs 22 by mechanically turning or physically dragging the prongs 22 while they are partially or wholly in a liquid state. A non-limiting example of this is the use of an oscillating or rotating severing means, e.g. hot wire, (not shown) to force or drag the prongs 22 to the desired azimuthal angle as the prongs 22 are cut. There will be many other methods of accomplishing this which will be apparent to one skilled in the art.

It should also be understood that an azimuthal angle may be imparted to the prongs 22 by using a combination of methods to bias the prongs 22. A nonlimiting example of the use of combinations of methods is the use of gravitational force and a pressure differential across the plane of the substrate 24 in combination to impart an azimuthal angle to the prongs 22. Another non-limiting example is the use of gravitational forces and a rotating severing means in combination to impart an azimuthal angle to the prongs 22. Many other methods of imparting an azimuthal angle to the prongs 22 will be apparent to one skilled in the art, as will the various combinations of methods.

ILLUSTRATIVE ARTICLE OF USE

Figure 6:
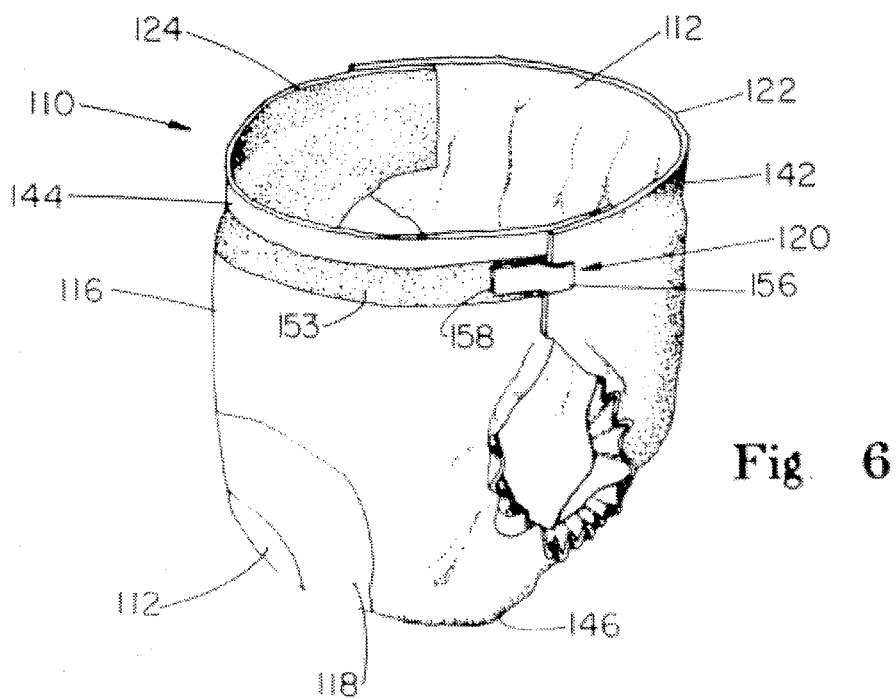
FIG. 6 is a perspective view of a disposable absorbent garment utilizing the fastening system of the present invention, showing the topsheet and core partially in cutaway.

An illustrative and nonlimiting example of the usage of the fastening system 120 of the present invention in an article of manufacture follows and is illustrated in FIG. 6. Mechanical fastening systems have been advantageously used in disposable absorbent articles as disclosed in U.S. patent application Ser. No. 07/132,281, Issue Batch No. N97, filed on Dec. 18, 1987, in the name of Scripps, which application is incorporated herein by reference for the purpose of showing a diaper 110 structure and the advantageous utilization of mechanical fastening systems 20 in such diaper 120 structures.

It is known, for example, that mechanical fastening systems 120 are less easily contaminated by oils and powders than are adhesive tape fastening systems and, further, may be easily reused. All of these features provide advantages when applied to a disposable diaper 110 intended for use on an infant. Also, a refastenable fastening system provides the advantage that the infant may be checked to see if soiling of the disposable diaper 110 has occurred during the wearing period.

Referring to FIG. 6, there is shown a disposable diaper 110 intended to be worn about the lower torso by an infant. As used herein, the term "disposable absorbent article" refers to a garment generally worn by infants or incontinent persons and which is drawn between the legs, fastened about the waist of the wearer and intended to be discarded after a single use and not to be laundered or restored. A "disposable diaper" is a particular disposable article intended and scaled to be worn by an infant.

A preferred diaper 110 comprises a liquid pervious topsheet 112, a liquid impervious backsheet 116, and an absorbent core 118 intermediate the topsheet 112 and backsheet 116. The topsheet 112 and backsheet 116 are at least partially peripherally joined to ensure the core 118 is held in position. The diaper 110 elements may be assembled in a variety of configurations well known to one skilled in the art, with a preferred configuration being generally described in U.S. Pat. No. 3,860,003 issued Jan. 14, 1975 to Buell, which patent is incorporated herein by reference for the purpose of disclosing a particularly preferred diaper 110 configuration.

The topsheet 112 and backsheet 116 of the diaper 110 are generally coextensive and at least partially peripherally joined together as noted above. Joining of the topsheet 112 and backsheet 116 may be accomplished by a hot-melt adhesive, such as Eastobond A3 manufactured by the Eastman Chemical Products Company of Kingsport, Tenn. The absorbent core 118 has length and width dimensions generally less than that of the topsheet 112 and backsheet 116. The core 118 is interposed between the topsheet 112 and backsheet 116 in fixed relationship.

The diaper 110 periphery comprises oppositely disposed first and second ends 122 and 124. The diaper 110 has a first waist portion 142 and a second waist portion 144 extending respectively from the first end 122 and second end 124 of the diaper 110 periphery towards the lateral centerline of the diaper 110 a distance of about one-fifth to about one-third the length of the diaper 110. The waist portions 142 and 144 comprise those portions of the diaper 110 which, when worn, encircle the waist of the wearer and are generally at the highest elevation of the diaper 110 when the wearer is in the standing position. The crotch 146 of the diaper 110 is that portion of the diaper 110 disposed between the first and second waist portions 142 and 144 and which, when worn is positioned between the legs of the wearer.

The absorbent "core" is any means for absorbing and retaining liquid body exudates. The absorbent core 118 is generally compressible, conformable, and nonirritating to the skin of the wearer. A preferred core 118 has first and second opposed faces and may, if desired, be further encased by tissue layers. One opposed face of the core 118 is oriented towards the topsheet 112 and the other opposed face is oriented towards the backsheet 116.

The absorbent core 118 is superimposed on the backsheet 116 and preferably joined thereto by any means well known in the art such as adhesive bonding. In a particularly preferred embodiment, adhesive bonding is accomplished by longitudinal adhesive bands which join the core 118 to the backsheet 116. The backsheet 116 is impervious to liquids and prevents liquids absorbed by and contained in the absorbent core 118 from wetting undergarments, clothing, bedding and any other objects which contact the diaper 110. As used herein, the term "backsheet" refers to any barrier disposed outwardly of the core 118 as the diaper 110 is worn and which contains absorbed liquids within the diaper 110. Preferably, the backsheet 116 is a polyolefinic film of about 0.012 to about 0.051 mm (0.0005–0.002 inches) in thickness. A polyethylene film is particularly preferred, with a suitable film being manufactured by the Monsanto Company of St. Louis, Mo. as film No. 8020. If desired, the backsheet 116 may be embossed or matte finished to provide a more clothlike appearance or be provided with passages to permit escape of vapors.

The topsheet 112 is compliant, tactily pleasing and nonirritating to the wearer's skin. The topsheet 112 prevents contact of the absorbent core 118 and liquids therein with the skin of the wearer. The topsheet 112 is liquid pervious, permitting liquids to readily penetrate therethrough. As used herein, the term "topsheet" refers to any liquid pervious facing which contacts the skin of the wearer while the diaper 110 is being worn and prevents the core 118 from contacting the skin of the wearer. The topsheet 112 may be made of woven, nonwoven, spunbonded or carded materials. A preferred topsheet 112 is carded and thermally bonded by means to those skilled in the nonwoven fabrics art. A particularly preferred topsheet 112 has a weight of about 18 to about 25 grams per square meter, a minimum dry tensile strength of about 400 grams per centimeter in the machine direction and a wet tensile strength of at least about 55 grams per centimeter in the cross-machine direction.

The diaper 110 is provided with a fastening system 120 and receiving surface 153 for maintaining the first waist portion 142 and second waist portion 144 in an overlapping configuration when the diaper 110 is worn, so that the diaper 110 is secured to the wearer. Thus, the diaper 110 is fitted to the wearer and a side closure is formed when the fastening system 120 is secured to the receiving surface 153.

The fastening system 120 should resist the separation forces which occur during the wearing period. The term "separation forces" refers to forces acting on the fastening system 120 and receiving surface 153 which tend to cause separation, release or removal of the fastening system 120 from the receiving surface 153. Separation forces include both shear and peel forces. The term "shear force" refers to distributive forces acting generally tangential to the receiving surface 153 and which may be thought of as being generally parallel to the plane of the substrate of the fastening system 120. The term "peel forces" refers to distributive forces acting in the generally longitudinal direction, and perpendicular to the plane of the receiving surface 153 and fastening system 120 substrates.

Shear forces are measured by tensile pulling of the fastening system 120 and receiving surface 153 in opposite directions generally parallel to the planes of the respective substrates. The method used to determine the resistance of a fastening system 120 and receiving surface 153 to shear forces is more fully set forth in U.S. Pat. No. 4,699,622 issued Oct. 13, 1987, to Toussant et al., which patent is incorporated herein by reference for the purpose of describing the measurement of shear forces.

Peel forces are measured by tensile pulling of the fastening system 120 from the receiving surface 153 at an included angle of about 135°. The method used to determine the resistance of a fastening system 120 and receiving surface 153 to peel forces is more fully set forth in U.S. patent application Ser. No. 07/132,281, Issue Batch No. N87, filed Nov. 18, 1987 in the name of Scripps, which application is incorporated herein by reference for the purpose of describing the measurement of peel forces.

Separation forces are typically generated by movements of the wearer or by the wearer trying to unfasten the diaper 110. Generally, an infant should not be able to unfasten or remove a diaper 110 the infant is wearing, nor should the diaper 110 come unfastened in the presence of ordinary separation forces which occur during normal wearing. However, an adult should be able to remove the diaper 110 to change it when soiled or check to see if soiling has occurred. Generally, the fastening system 120 and receiving surface 153 should resist a peel force of at least 200 grams, preferably at least about 500 grams, and more preferably, at least about 700 grams. Furthermore, the fastening system 120 and receiving surface 153 should resist a shear force of at least 500 grams, preferably at least about 750 grams, and more preferably at least about 1,000 grams.

The receiving surface 153 may be disposed in a first position anywhere on the diaper 110, so long as the receiving surface 153 engages the fastening means to maintain the first and second waist portions 144 in an overlapping configuration. For example, the receiving surface 153 may be disposed on the outside surface of the second waist portion 144, on the inside surface of the first waist portion 142, or any other position on the diaper 110 on which it is disposed so as to engage with the fastening system 120. The receiving surface 153 may be integral, a discrete element joined to the diaper 110, or a single piece of material that is neither divided or discontinuous with an element of the diaper 110, such as the topsheet 112 or backsheet 116.

While the receiving surface 153 may assume various sizes and shapes, the receiving surface 153 preferably comprises one or more integral patches positioned across the outside surface of the second waist portion 144 to allow for maximum fit adjustment at the waist of the wearer. As illustrated in FIG. 6, the receiving surface 153 is preferably an elongate rectangularly shaped integral member secured to the outer surface of the second waist portion 144.

A suitable receiving surface 153 is a nonwoven fabric, is stitchbonded or any other type of fiber or loop material well known in the art. The receiving surface 153 may be manufactured from a variety of materials which provide fiber elements, and preferably loops capable of being intercepted and retained by the engaging means. Suitable materials include nylon, polyester, polypropylene and combinations of the foregoing. A suitable receiving surface 153 comprises a number of fiber loops projecting from a woven and is commercially available as Scotchmate brand nylon woven loop No. FJ3401, sold by the Minnesota Mining and Manufacturing Company of St. Paul, Minn. Another suitable receiving surface 153 comprises a tricot having a plurality of nylon filament loops projecting from a nylon backing and is commercially available from Gilford Mills of Greensboro, N.C. and designated Gilford No. 16110. A particularly preferred receiving surface is stitchbonded loop material sold by the Milliken Company of Spartanburg, S.C. under Number 970026.

The fastening system 120 is intended to engage the complementary receiving surface 153 to provide a secure fit for the diaper 110. The fastening system 120 may comprise any of the well known configurations utilized for achieving a side closure on a disposable diaper 110. The fastening system 120 substrate is joined to the diaper 110 in spaced relationship from the receiving means 153. As shown on FIG. 6, the fastening system 120 is preferably disposed on both the first and second longitudinal sides of the diaper 110. A preferred configuration for the fastening system 120 minimizes any potential contact between the prongs of the fastening system 120 and the skin of the wearer. A preferred fastening system 120 disposition is a Y-shaped tape arrangement, described in detail in U.S. Pat. No. 3,848,594 issued Nov. 19, 1974 to Buell. An alternatively preferred fastening system 120 arrangement is described in detail in U.S. Pat. No. 4,699,622 issued Oct. 13, 1987 to Toussant et al., both of which patents are incorporated herein by reference for the purpose of illustrating various placements of the fastening system 120 on the disposable diaper 110.

The fastening system 120 of FIG. 6 has a manufacturer's end 156 and an oppositely disposed user's end 158. The manufacturer's end 156 is joined to the diaper 110, preferably in juxtaposition with the first waist portion 142. The user's end 158 is the free end and is secured to the receiving surface 153 when the diaper 110 is secured to the wearer.

After the diaper 110 is fitted about the waist of the wearer, the user's end 158 of the fastening system 120 is releasably secured to the receiving surface 153, and preferably positioned on the second waist portion 144, thereby causing the diaper 110 to encircle the waist of the wearer. The diaper 110 has now effected a side closure. The prongs (not shown) extend from the fastening system 120 of the user's end 158 so that the prong engaging means intercept the strands of the receiving surface 153.

A fastening system 120 and complementary receiving surface 153 which provides a resistance to peel forces in excess of 700 grams and a resistance to shear forces in excess of 1,000 grams may be constructed as follows according to the specific parameters of the fastening system 120 set forth in the aforementioned "Process of Manufacture." The complementary receiving surface 153 used in conjunction with the fastening system 120 is the aforementioned Milliken Company No. 970026 stitchbonded loop fabric.

The fastening system 120 is at least about 2.54 centimeters (1 inch) in width and may be of any length which provides a convenient user's end 158, with a length of at least about 3.5 centimeters (1.4 inches) being preferred. The array of the prongs of fastening system 120 comprises a matrix having about 26 prongs per square centimeter (169 prongs per square inch). The prongs are preferentially oriented in substantially the same direction and face the user's end 158 of the fastening tape.

In use, the diaper 110 is applied to the wearer by positioning the first waist portion 142 around the wearer's back and drawing the remainder of the diaper 110 between the legs of the wearer so that the second waist portion 144 is disposed across the front of the wearer. The user's ends 158 of the fastening system 120 are then secured to the receiving surface 153 on the outside surface of the second waist portion 144 to form a side closure.

What is claimed is:

1. An article having a machine direction and a cross-machine direction comprising:

a substrate; and a fastening system for attaching to a complimentary receiving surface, said fastening system comprising a multiplicity of prongs, each said prong comprising:

a shank joined to said substrate at a base, said shank having a proximal end contiguous with said base and projecting outwardly from said substrate, said shank being nonperpendicularly oriented relative to the plane of said substrate, said shank further having an azimuthal angle between about 20° and about 160°; and an engaging means joined to said shank and projecting laterally beyond the periphery of said shank.

2. The article of claim 1 wherein said shank has an azimuthal angle ranging from about 45° to about 135°.

3. The article of claim 1 wherein said shank has an azimuthal angle ranging from about 60° to about 120°.

4. The article of claim 1 wherein said shank has an azimuthal angle of about 90°.

5. The article of claim 1 wherein each said prong additionally comprises a shank having a leading angle and a trailing angle, said leading angle being substantially different from said trailing angle.

6. An absorbent article comprising:

a topsheet;

a backsheet joined with said topsheet;

an absorbent core positioned between said topsheet and said backsheet; and a fastening system comprising:

a substrate; and a multiplicity of prongs, each said prong comprising:

a shank joined to said substrate at a base, said shank having a proximal end contiguous with said base and projecting outwardly from said substrate, said shank being nonperpendicularly oriented relative to the plane of said substrate, said shank further having an azimuthal angle between about 20° and about 160°; and an engaging means joined to said shank and projecting laterally beyond the periphery of said shank.

7. The absorbent article of claim 6, further comprising a complementary loop fastening material comprising at least one fibrous element, said loop fastening material being joined to said outer cover such that at least one of said prongs of said fastening system is capable of mechanically entangling said fibrous element.

8. The absorbent article of claim 6, further comprising a tape having a first end and a second end, said first end being joined to said outer cover and said fastening system being joined to said second end.

9. The absorbent article of claim 8, further comprising a complementary loop fastening material comprising at least one fibrous element, said loop fastening material being joined to said outer cover such that at least one of said prongs of said fastening system is capable of mechanically entangling said fibrous element.

10. An absorbent article comprising:

an outer cover comprising a liquid pervious topsheet and a liquid impervious backsheet joined to said topsheet;

an absorbent core positioned between said topsheet and said backsheet; and a fastening system joined to said outer cover, said fastening system comprising:

a substrate; and a multiplicity of prongs, each said prong comprising:

a shank joined to said substrate at a base, said shank having a proximal end contiguous with said base and projecting outwardly from said substrate, said shank having a leading angle and a trailing angle, said leading angle being substantially different from said trailing angle, said shank being nonperpendicularly oriented relative to the plane of said substrate, said shank further having an azimuthal angle between about 20° and about 160°; and an engaging means joined to said shank and projecting laterally beyond the periphery of said shank.

11. The absorbent article of claim 10 wherein said shank has an azimuthal angle ranging from about 45° to about 135°.

12. The absorbent article of claim 10 wherein said shank has an azimuthal angle ranging from about 60° to about 120°.

13. The absorbent article of claim 10 wherein said shank has an azimuthal angle of about 90°.

14. The absorbent article of claim 10 wherein said substrate of said fastening system comprises at least a portion of said outer cover.

15. The absorbent article of claim 10 additionally comprising a pair of tapes, each of said tapes comprising a first end and a second end, said first end being joined to said outer cover and said second end having said fastening system joined thereto.

16. The absorbent article of claim 15 wherein said shank has an azimuthal angle ranging from about 45° to about 135°.

17. The absorbent article of claim 15 wherein said shank has an azimuthal angle ranging from about 60° to about 120°.

18. The absorbent article of claim 15 wherein said shank has an azimuthal angle of about 90°.

19. The absorbent article of claim 15 wherein at least a portion of said second end of each of said tapes forms said substrate of said fastening system.

* * * * *

UNITED STATES PATENT AND TRADEMARK OFFICE
CERTIFICATE OF CORRECTION

PATENT NO. : 5,540,673

DATED : July 30, 1996

INVENTOR(S) : Dennis A. Thomas et al.

It is certified that error appears in the above-identified patent and that said Letters Patent is hereby corrected as shown below:

| | |
|---|---|
| Column 6, line 11 | delete "otherwise-specified" and insert --otherwise specified-- |
| Column 10, line 67 | after "substrate" insert --24.--. |
| Column 12, line 61 | delete "manufacture/the" and insert --manufacture the--. |
| Column 13, line 14 | delete "Riddleton" and insert --Middleton--. |
| Column 15, line 63 | after 'result' delete "," and insert --.--. |
| Column 16, line 28 | delete "Riddleton" and insert --Middleton--.. |
| Column 18, line 33 | delete "Rote" and insert --More--. |
| Column 22, line 5 | delete "180' and insert --180°--. |

Signed and Sealed this

Twenty-third Day of February, 1999

Attest:

Q. TODD DICKINSON

*Attesting Officer*    *Acting Commissioner of Patents and Trademarks*